United States Patent
Krohn et al.

(10) Patent No.: US 11,883,518 B2
(45) Date of Patent: Jan. 30, 2024

(54) METHOD FOR DYEING KERATINOUS MATERIAL, COMPRISING THE USE OF AN ORGANOSILICON COMPOUND, AN HYDROXYCARBOXYLIC ACID ESTER, A DIOL AND A DYEING COMPOUND

(71) Applicant: Henkel AG & Co. KGaA, Duesseldorf (DE)

(72) Inventors: Rene Krohn, Norderstedt (DE); Thomas Hippe, Appen (DE); Jessica Brender, Hamburg (DE); Stefan Hoepfner, Hamburg (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/785,878

(22) PCT Filed: Oct. 16, 2020

(86) PCT No.: PCT/EP2020/079186
§ 371 (c)(1),
(2) Date: Jun. 15, 2022

(87) PCT Pub. No.: WO2021/121723
PCT Pub. Date: Jun. 24, 2021

(65) Prior Publication Data
US 2023/0059044 A1 Feb. 23, 2023

(30) Foreign Application Priority Data
Dec. 16, 2019 (DE) .......................... 102019219708.6

(51) Int. Cl.
*A61Q 5/10* (2006.01)
*A61K 8/58* (2006.01)
*A61K 8/34* (2006.01)
*A61K 8/37* (2006.01)

(52) U.S. Cl.
CPC .............. *A61K 8/585* (2013.01); *A61K 8/345* (2013.01); *A61K 8/37* (2013.01); *A61Q 5/10* (2013.01); *A61K 2800/432* (2013.01); *A61K 2800/884* (2013.01); *A61K 2800/95* (2013.01)

(58) Field of Classification Search
CPC .......... A61K 8/585; A61K 8/345; A61K 8/37; A61K 2800/432; A61K 2800/884; A61K 2800/95; A61Q 5/10; A61Q 5/065
USPC ............................................................. 8/405
See application file for complete search history.

(56) References Cited

U.S. PATENT DOCUMENTS

2010/0083446 A1* 4/2010 Brun ....................... A61K 8/891
8/405

FOREIGN PATENT DOCUMENTS

| DE | 102018207025 A1 | * | 11/2019 | ............... A61Q 5/10 |
| DE | 102018218647 A1 | * | 4/2020 | ............... A61Q 5/00 |
| DE | 102018218654 A1 | * | 4/2020 | ............... A61Q 5/06 |
| EP | 2168633 A2 | | 3/2010 | |

OTHER PUBLICATIONS

George Wypych: "Plasticizers Use and Selection for Specific Polymers", In: "Handbook of Plasticizers", Jan. 1, 2017 (Jan. 1, 2017), Elsevier, XP055758495, ISBN:978-1-895198-97-3, Seiten 333-483, DOI: 10.1016/B978-1-895198-97-3.50013-5, Seite 357—Seite 361.

* cited by examiner

*Primary Examiner* — Eisa B Elhilo
(74) *Attorney, Agent, or Firm* — Lorenz & Kopf, LLP

(57) ABSTRACT

The subject of the present disclosure is a method for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms, and
(a2) at least one hydroxycarboxylic acid ester,
(a3) at least one diol and
Application of an agent (b) to the keratinous material, wherein the agent (b) comprises:
(b1) at least one sealing reagent,
wherein at least one of the agents (a) and (b) further comprises at least one colorant compound selected from the group of pigments and/or direct dyes.

20 Claims, No Drawings

METHOD FOR DYEING KERATINOUS MATERIAL, COMPRISING THE USE OF AN ORGANOSILICON COMPOUND, AN HYDROXYCARBOXYLIC ACID ESTER, A DIOL AND A DYEING COMPOUND

CROSS-REFERENCE TO RELATED APPLICATION

This application is a U.S. National-Stage entry under 35 U.S.C. § 371 based on International Application No. PCT/EP2020/079186, filed Oct. 16, 2020, which was published under PCT Article 21(2) and which claims priority to German Application No. 102019219708.6, filed Dec. 16, 2019, which are all hereby incorporated in their entirety by reference.

TECHNICAL FIELD

The subject of the present application is a method for treating keratinous material, in particular human hair, which comprises the application of two agents (a) and (b). Agent (a) is exemplified by its content of at least one organic silicon compound (a1), at least one hydroxycarboxylic acid ester (a2) and at least one diol (a3). The agent (b) contains at least one sealing reagent (b1). Furthermore, either agent (a) or agent (b) or both agents (a) and (b) contain at least one colorant compound selected from the group of pigments and/or direct dyes.

A further subject of this application is a multi-component packaging unit (kit-of-parts) for dyeing keratinous material, in particular human hair, which comprises at least three separately prepared agents (a'), (a") and (b). Agents (a') and (a") can be used to prepare the agent (a) used in the process described above.

Still another subject of this application is a multi-component packaging unit (kit-of-parts) for dyeing keratinous material, in particular human hair, which comprises separately assembled at least four agents (a'), (a"), (a''') and (b). Agents (a'), (a") and (a''') can be used to prepare agent (a) used in the process described above.

Also a further subject of this application is a multi-component packaging unit (kit-of-parts) for dyeing keratinous material, in particular human hair, which comprises separately prepared at least five agents (a'), (a"), (a'''), (b') and (b"). From the agents (a'), (a") and (a'''), the agent (a) used in the above-described method can be prepared, and from the agents (b') and (b"), the agent (b) used in the above-described method can be prepared.

BACKGROUND

Changing the shape and color of keratinous fibers, especially hair, is an important area of modern cosmetics. To change the color of the hair, the professional knows various coloring systems, depending on the requirements of coloring. For permanent, intensive dyeings with good fixing properties and good gray coverage, oxidation dyes are usually used. Such colorants usually contain oxidation dye precursors, so-called developer components and coupler components, which form the actual dyes under the influence of oxidizing agents such as hydrogen peroxide. Oxidation dyes are exemplified by very long-lasting dyeing results.

When using direct dyes, already formed dyes are transmitted from the colorant into the hair fiber. Compared to oxidative hair dyeing, the dyeings obtained with direct dyes have lower durability and faster washout. Dyes with direct dyes usually remain on the hair for a period of between 5 and about 20 washes.

For short-term color changes on the hair and/or skin, the use of color pigments is known. Color pigments are generally understood to be insoluble, color-imparting substances. These are present undissolved in the form of small particles in the coloring formulation and are merely deposited externally on the hair fibers and/or skin surface. Therefore, they can usually be removed without residue by a few washes with surfactant-containing cleaning agents. Various products of this type are available on the market under the name of hair mascara.

If the user desires particularly long-lasting colorations, the use of oxidative colorants has so far been his only option. However, despite multiple optimization attempts, an unpleasant ammonia odor or amine odor cannot be completely avoided during oxidative hair coloring. The hair damage still associated with the use of the oxidative dyes also has a detrimental effect on the user's hair.

EP 2168633 B1 deals with the task of producing long-lasting hair colorations using pigments. The paper teaches that when the combination of a pigment, an organic silicon compound, a film-forming polymer and a solvent is used on hair, it is possible to produce colorations that are particularly resistant to friction and/or shampooing.

BRIEF SUMMARY

Methods for dyeing keratinous material and kits-of-parts for the same are provided. In an exemplary embodiment, a method for dyeing keratinous material includes applying an agent to the keratinous material, where the agent includes an organic silicon compound (a1), a hydroxycarboxylic acid ester (a2), and a diol (a3). The organic silicon compound is a silane with one, two, or three silicon atoms. An agent (b) is also applied to the keratinous material, where the agent (b) includes a sealing agent. At least one of agents (a) and (b) also include a colorant compound selected from pigments and/or direct dyes.

A kit-of-parts for dyeing keratinous material is provided in another exemplary embodiment. The kit-of-parts includes a first container containing an agent (a'), a second container containing an agent (a"), a third container containing an agent (a'''), and a fourth container containing an agent (b). The agent (a') includes an organic silicon compound (a1) selected from silanes having one, two, or three silicon atoms. The agent (a") includes a hydroxycarboxylic acid ester (a2), and the agent (a''') includes a diol (a3). The agent (b) includes a sealing reagent (b1). At least one of the agents (a"), (a''') and (b) also includes a colorant selected from pigments and/or direct dyes.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The great advantage of the organic silicon compound-based dyeing principle is that the high reactivity of this class of compounds enables very fast treatment. This means that extremely good coloring results can be achieved after very short application periods of just a few minutes. In addition to these advantages, however, the high reactivity of alkoxysilanes also has some disadvantages.

Due to their high reactivity, the organic silicon compounds used cannot be prepared together with larger amounts of water, since a large excess of water initiates immediate hydrolysis followed by polymerization. The polymerization that takes place during storage of the organic silicon compound in the aqueous agent manifests itself in thickening or gelation of the aqueous preparation. This makes the preparations so highly viscous, gelatinous or gelatinous that they can no longer be applied evenly to the keratin material. In addition, the storage of the organic silicon compounds used in the presence of high amounts of water is associated with a loss of their reactivity, so that the formation of a resistant coating on the keratin material is also no longer possible.

For these reasons, it is necessary to store the organic silicon compounds in an anhydrous or low-water environment and to prepare the corresponding preparations in a separate container. Due to their high reactivity, the organic silicon compounds can react not only with water but also with other cosmetic ingredients. To avoid all undesirable reactions, the preparations with organic silicon compounds therefore preferably contain no other ingredients or only the selected ingredients that have proven to be chemically inert to the organic silicon compounds. Accordingly, the concentration of organic silicon compounds in the preparation is preferably chosen to be relatively high. The low-water preparations, which contain the organic silicon compounds used in relatively high concentrations, can also be referred to as "silane blends".

For application to the keratin material, the user must now convert this relatively highly concentrated silane blend into a ready-to-use mixture. In this ready-to-use mixture, on the one hand the concentration of organic silicon compounds is lowered, and on the other hand the application mixture also contains a higher proportion of water (or an alternative ingredient), which triggers the polymerization leading to the coating.

It has proved extremely challenging to optimally adapt the polymerization rate, i.e. the speed at which the coating forms on the keratin material, to the application conditions.

When applied to human hair, for example, a polymerization rate that is too fast will result in polymerization being completed before all hair sections have been treated. Too rapid polymerization therefore makes whole-head treatment impossible. In the coloring process, the excessively fast polymerization manifests itself in an uneven color result, so that the hair sections that were treated last are inadequately colored.

There is a need to provide hair dyes with pigments that on the one hand have high wash and rub fastness and on the other hand do not negatively affect hair properties such as manageability and feel. For this purpose, it would be desirable to be able to adapt the polymerization rate of the organic silicon compounds used to the conditions of application, in particular to the conditions prevailing when applied to the human head. In other words, a process was sought by which the organic silicon compounds used would remain reactive long enough to allow whole-head treatment without unduly extending the application period.

Surprisingly, it has now been found that the aforementioned task can be excellently solved if keratinous materials, in particular human hair, are colored by a process in which at least two agents (a) and (b) are applied to the keratinous materials (hair). Here, the first agent (a) contains at least one organic silicon compound from the group of silanes with one, two or three silicon atoms, at least one hydroxycarboxylic acid ester (a2) and further a diol (a3). The second agent (b) contains at least one sealing reagent (b1).

Surprisingly, when the two agents (a) and (b) were used in a dyeing process, the reactivity of the organic silicon compounds (a1) was thus optimally adapted to the application conditions prevailing in a whole-head hair dyeing process. Even more complicated or time-consuming dyeing techniques could be realized when using the process. When the two agents (a) and (b) were used in a dyeing process on keratin material, in particular on human hair, in this way it was possible to produce dyeings with particularly high uniformity, rub fastness and wash fastness.

A first object of the present disclosure is a method for coloring keratinous material, in particular human hair, comprising the following steps:

Application of an agent (a) to the keratinous material, wherein the agent (a) comprises:
(a1) at least one organic silicon compound selected from the group of silanes having one, two or three silicon atoms,
(a2) at least one hydroxycarboxylic acid ester,
(a3) at least one diol and
Application of an agent (b) to the keratinous material, wherein the agent (b) comprises:
(b1) at least one sealing reagent,
wherein at least one of the agents (a) and (b) further comprises at least one colorant compound selected from the group of pigments and/or direct dyes.

In the work leading to the present disclosure, it has been found that the preferential successive application of agents (a) and (b) enables the production of very stable and washfast colorations on the keratinous materials. Without being limited to this theory, it is assumed in this context that the joint application of organic silicon compound (a1) and hydroxycarboxylic acid ester (a2) leads to the formation of a particularly resistant film on the keratinous material. Application of the second agent (b) seals the film applied to the keratinous material, making it more resistant to washing and/or friction. By incorporating at least one colorant compound selected from the group of pigments and/or direct dyes into at least one of agents (a) and (b), colored films can be obtained.

In this way, the colorant compounds can be permanently fixed to the keratinous material, so that extremely washfast colorations with good resistance to friction and/or shampooing could be obtained.

With the aid of the hydroxycarboxylic acid ester (a2) and the diol (a3), it was also possible, in particular, to optimally adapt the oligo and polymerization rate of the organic silicon compound (a1), i.e. the rate at which the silane film forms on the keratin material, to the application conditions.

Keratinous Material

Keratinous material means hair, the skin, the nails (such as fingernails and/or toenails). Furthermore, wool, fur and feathers also fall under the definition of keratinous material.

Preferably, keratinous material is understood to mean human hair, human skin and human nails, in particular fingernails and toenails. Most preferably, keratinous material is understood to mean human hair.

Agents (a) and (b)

In the process described, agents (a) and (b) are applied to the keratinous material, in particular human hair. The two agents (a) and (b) are different from each other.

In other words, a first object of the present disclosure is a method for treating keratinous material, in particular human hair, comprising the following steps:

Application of an agent (a) to the keratinous material, wherein the agent (a) comprises:
(a1) at least one organic silicon compound selected from the group of silanes having one, two or three silicon atoms,
(a2) at least one hydroxycarboxylic acid ester,
(a3) at least one diol and
Application of an agent (b) to the keratinous material, wherein the agent (b) comprises:
(b1) at least one sealing reagent,
wherein at least one of the agents (a) and (b) further comprises at least one colorant compound selected from the group of pigments and/or direct dyes.

Agent (a)

Agent (a) contains ingredients (a1), (a2) and (a3) essential to the present disclosure.

Agent (a) may contain the three ingredients (a1), (a2) and (a3) in a cosmetic carrier, particularly preferably in an aqueous or aqueous-alcoholic cosmetic carrier. This cosmetic carrier can be liquid, gel or cream. Pasty, solid or powdery cosmetic carriers can also be used for the preparation of agent (a). For the purpose of hair treatment, in particular hair coloring, such carriers are, for example, creams, emulsions, gels or also surfactant-containing foaming solutions, such as shampoos, foam aerosols, foam formulations or other preparations suitable for application to the hair.

Preferably, the cosmetic carrier contains—based on its weight—at least about 2% by weight of water. Further preferably, the water content is above about 10% by weight, still further preferably above about 20% by weight and particularly preferably above about 40% by weight. The cosmetic carrier can also be aqueous-alcoholic. For the purposes of the present disclosure, aqueous alcoholic solutions are understood to mean aqueous solutions containing about 2 to about 70% by weight of a $C_1$-$C_4$ alcohol, in particular ethanol or isopropanol.

Alternatively, agent (a) is anhydrous or low in water. In this embodiment, agent (a) comprises a maximum of about 5% by weight of water, based on its weight. Further preferably, the water content of the agent (a) is below about 3% by weight, still further preferably below about 2% by weight and particularly preferably below about 1% by weight.

Organic Silicon Compounds from the Group of Silanes (a1)

As an ingredient (a1) essential to the present disclosure, the composition (a) contains at least one organic silicon compound from the group of silanes having one, two or three silicon atoms.

Particularly preferably, the agent (a) contains at least one organic silicon compound (a1) selected from silanes having one, two or three silicon atoms, the organic silicon compound comprising one or more hydroxyl groups and/or hydrolyzable groups per molecule.

These organic silicon compounds (a1) or organic silanes contained in the agent (a) are reactive compounds.

Organic silicon compounds, alternatively referred to as organosilicon compounds, are compounds that either have a direct silicon-carbon (Si—C) bond or in which the carbon is attached to the silicon atom via an oxygen, nitrogen or sulfur atom. The organic silicon compounds of the present disclosure are compounds containing one to three silicon atoms. Particularly preferably, the organic silicon compounds contain one or two silicon atoms.

According to the IUPAC rules, the term silane stands for a group of substances of chemical compounds based on a structure of silicon and hydrogen. In organic silanes, the hydrogen atoms are wholly or partially replaced by organic groups such as (substituted) alkyl groups and/or alkoxy groups. In the organic silanes, some of the hydrogen atoms may also be replaced by hydroxy groups.

In a particularly preferred embodiment, a method is exemplified by the application of an agent (a) to the keratinous material, said agent (a) comprising at least one organic silicon compound (a1) selected from silanes having one, two or three silicon atoms, said organic silicon compound further comprising one or more hydroxyl groups or hydrolyzable groups per molecule.

In a very particularly preferred embodiment, a method is exemplified by the application of an agent (a) to the keratinous material, said agent (a) comprising at least one organic silicon compound (a1) selected from silanes having one, two or three silicon atoms, said organic silicon compound further comprising one or more basic chemical functions and one or more hydroxyl groups or hydrolyzable groups per molecule.

This basic group or basic chemical function can be, for example, an amino group, an alkylamino group, a dialkylamino group or a trialkylamino group, which is preferably connected to a silicon atom via a linker. Preferably, the basic group is an amino group, a $C_1$-$C_6$ alkylamino group or a di ($C_1$-$C_6$) alkylamino group.

The hydrolyzable group(s) is preferably a $C_1$-$C_6$ alkoxy group, in particular an ethoxy group or a methoxy group. It is preferred if the hydrolyzable group is directly bonded to the silicon atom. For example, if the hydrolyzable group is an ethoxy group, the organic silicon compound preferably contains a structural unit R'R"R'"Si—O—$CH_2$—$CH_3$. The radicals R', R" and R'" represent the three remaining free valences of the silicon atom.

A very particularly preferred method is exemplified wherein the agent (a) contains at least one organic silicon compound selected from silanes having one, two or three silicon atoms, the organic silicon compound preferably comprising one or more basic chemical functions and one or more hydroxyl groups or hydrolyzable groups per molecule.

Particularly good results were obtained when the agent (a) contains at least one organic silicon compound (a1) of the formula (I) and/or (II).

The compounds of formulae (I) and (II) are organic silicon compounds selected from silanes having one, two or three silicon atoms, wherein the organic silicon compound comprises one or more hydroxyl groups and/or hydrolyzable groups per molecule.

In another very particularly preferred embodiment, the method is exemplified wherein an agent is applied to the keratinous material (or human hair), the agent (a) comprising at least one organic silicon compound (a) of formula (I) and/or (II),

where
$R_1$, $R_2$ independently represent a hydrogen atom or a $C_1$-$C_6$ alkyl group,
L is a linear or branched, divalent $C_1$-$C_{20}$ alkylene group,
$R_3$ is a hydrogen atom or a $C_1$-$C_6$ alkyl group,
$R_4$ stands for a $C_1$-$C_6$ alkyl group
a, represents an integer from 1 to 3, and
b stands for the integer 3-a,

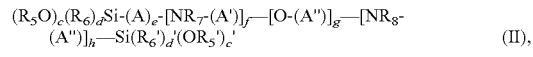

where
$R_5$, $R_{5'}$, $R_{5''}$ independently represent a hydrogen atom or a $C_1$-$C_6$ alkyl group, $R_6$, $R_{6'}$ and $R_{6''}$ independently of one another represent a $C_1$-$C_6$ alkyl group, A, A', A", A'" and A"" independently represent a linear or branched $C_1$-$C_{20}$ divalent alkylene group, $R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of formula (III)

$$(A'''')—Si(R_6'')_{d''}(OR_5'')_{c''} \qquad (III),$$

c, stands for an integer from 1 to 3,
d stands for the integer 3-c,
c' stands for an integer from 1 to 3,
d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
with the proviso that at least one of the radicals from e, f, g and h is different from 0.

The substituents $R_1$, $R_2$, $R_3$, $R_4$, $R_5$, $R_5'$, $R_5''$, $R_6$, $R_6'$, $R_6''$, $R_7$, $R_8$, L, A, A', A", A'" and A"" in the compounds of formula (I) and (II) are exemplified below:

Examples of a $C_1$-$C_6$ alkyl group include methyl, ethyl, propyl, isopropyl, n-butyl, s-butyl and t-butyl, n-pentyl and n-hexyl groups. Propyl, ethyl and methyl are preferred alkyl radicals. Examples of a $C_2$-$C_6$ alkenyl group are vinyl, allyl, but-2-enyl, but-3-enyl as well as isobutenyl, preferred $C_2$-$C_6$ alkenyl radicals are vinyl and allyl. Preferred examples of a hydroxy-$C_1$-$C_6$-alkyl group include a hydroxymethyl, a 2-hydroxyethyl, a 2-hydroxypropyl, a 3-hydroxypropyl, a 4-hydroxybutyl, a 5-hydroxypentyl and a 6-hydroxyhexyl group; a 2-hydroxyethyl group is particularly preferred. Examples of an amino-$C_1$-$C_6$-alkyl group are the aminomethyl group, the 2-aminoethyl group, the 3-aminopropyl group. The 2-aminoethyl group is particularly preferred. Examples of a linear divalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, divalent alkylene groups can also be branched. Examples of branched $C_3$-$C_{20}$ divalent alkylene groups are (—$CH_2$—CH($CH_3$)—) and (—$CH_2$—CH($CH_3$)—$CH_2$—).

In the organic silicon compounds of formula (I)

$$R_1R_2N\text{-}L\text{-}Si(OR_3)_a(R_4)_b \qquad (I),$$

$R_1$ and $R_2$ independently represent a hydrogen atom or a $C_1$-$C_6$ alkyl group. Very preferably, $R_1$ and $R_2$ both represent a hydrogen atom.

In the middle part of the organic silicon compound is the structural unit or linker -L- which stands for a linear or branched, divalent $C_1$-$C_{20}$ alkylene group.

A divalent $C_1$-$C_{20}$ alkylene group may alternatively be referred to as a divalent or divalent $C_1$-$C_{20}$ alkylene group, by which is meant that each L grouping may form two bonds. One bond is from the amino group $R_1R_2N$ to the linker L, and the second bond is between the linker L and the silicon atom.

Preferably, -L- represents a linear, divalent (i.e., divalent) $C_1$-$C_{20}$ alkylene group. Further preferably, -L- represents a linear divalent $C_1$-$C_6$ alkylene group. Particularly preferably, -L- stands for a methylene group (—$CH_2$—), an ethylene group (—$CH_2$—$CH_2$—), a propylene group (—$CH_2$—$CH_2$—$CH_2$—) or a butylene group (—$CH_2$—$CH_2$—$CH_2$—$CH_2$—). Very preferably, L represents a propylene group (—$CH_2$—$CH_2$—$CH_2$—).

The linear propylene group (—$CH_2$—$CH_2$—$CH_2$—) can alternatively be referred to as the propane-1,3-diyl group.

The organic silicon compounds of formula (I)

$$R_1R_2N\text{-}L\text{-}Si(OR_3)_a(R_4)_b \qquad (I),$$

each carry at one end the silicon-containing grouping —Si$(OR_3)_a(R_4)_b$.

In the terminal structural unit —Si$(OR_3)_a(R_4)_b$, $R_3$ is hydrogen or $C_1$-$C_6$ alkyl, and $R_4$ is $C_1$-$C_6$ alkyl. Particularly preferably, $R_3$ and $R_4$ independently represent a methyl group or an ethyl group.

Here, a represents an integer from 1 to 3, and b represents the integer 3-a. If a represents number 3, then b is 0. If a stands for number 2, then b is equal to 1. If a stands for number 1, then b is equal to 2.

Particularly resistant films could be produced if the agent (a) contains at least one organic silicon compound (a1) of the formula (I) in which the radicals $R_3$, $R_4$ independently of one another represent a methyl group or an ethyl group.

When using the process for dyeing keratinous material, dyeings with the best wash fastness could be obtained analogously when the agent (a) contains at least one organic silicon compound of formula (I) in which the radicals $R_3$, $R_4$ independently of one another represent a methyl group or an ethyl group.

Furthermore, dyeings with the best wash fastness could be obtained if the agent (a) contains at least one organic silicon compound of the formula (I) in which the radical a represents number 3. In this case, the remainder b stands for number 0.

In a further preferred embodiment, the agent (a) used in the process is exemplified wherein it comprises at least one organic silicon compound (a1) of formula (I), wherein
$R_3$, $R_4$ independently represent a methyl group or an ethyl group, and
a stands for number 3 and
b stands for number 0.

In another preferred embodiment, a method is exemplified wherein the agent (a) comprises at least one organic silicon compound (a1) of formula (I), $$R_1R_2N\text{-}L\text{-}Si(OR_3)_a(R_4)_b \qquad (I),$$

where
$R_1$, $R_2$ both represent a hydrogen atom, and
L is a linear, divalent $C_1$-$C_6$ alkylene group, preferably a propylene group (—$CH_2$—$CH_2$—$CH_2$—) or an ethylene group (—$CH_2$—$CH_2$—),
$R_3$ represents a hydrogen atom, an ethyl group or a methyl group,
$R_4$ represents a methyl group or an ethyl group,
a stands for number 3 and
b stands for number 0.

Organic silicon compounds of the formula (I) which are particularly suitable for solving the problem as contemplated herein are

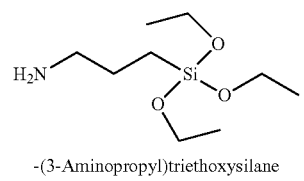

-(3-Aminopropyl)triethoxysilane

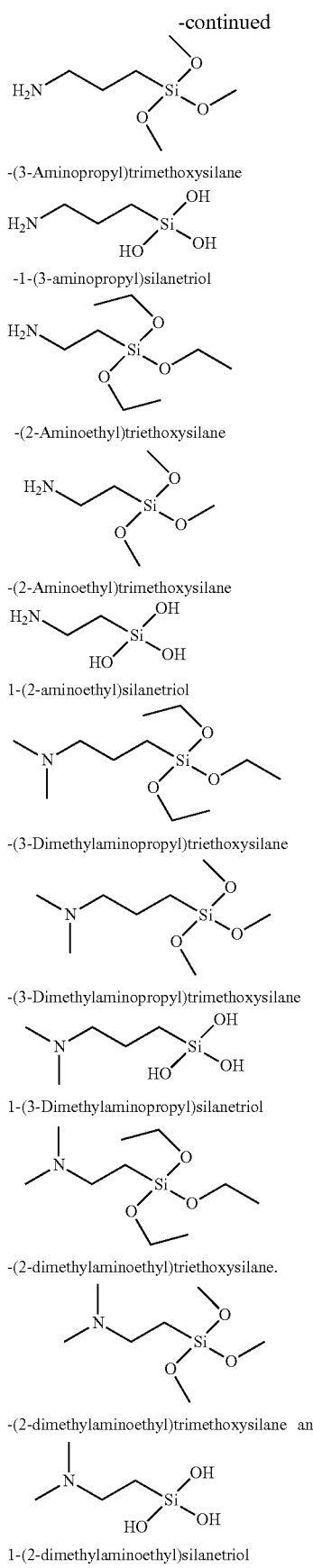

- -(3-Aminopropyl)trimethoxysilane
- -1-(3-aminopropyl)silanetriol
- -(2-Aminoethyl)triethoxysilane
- -(2-Aminoethyl)trimethoxysilane
- 1-(2-aminoethyl)silanetriol
- -(3-Dimethylaminopropyl)triethoxysilane
- -(3-Dimethylaminopropyl)trimethoxysilane
- 1-(3-Dimethylaminopropyl)silanetriol
- -(2-dimethylaminoethyl)triethoxysilane.
- -(2-dimethylaminoethyl)trimethoxysilane and
- 1-(2-dimethylaminoethyl)silanetriol In a further preferred embodiment, a method is exemplified wherein the agent (a) comprises at least one organic silicon compound (a1) selected from the group of:
(3-Aminopropyl)triethoxysilane
(3-Aminopropyl)trimethoxysilane
1-(3-aminopropyl)silanetriol
(2-Aminoethyl)triethoxysilane
(2-Aminoethyl)trimethoxysilane
1-(2-aminoethyl)silanetriol
(3-Dimethylaminopropyl)triethoxysilane
(3-Dimethylaminopropyl)trimethoxysilane
1-(3-Dimethylaminopropyl)silanetriol
(2-dimethylaminoethyl)triethoxysilane.
(2-dimethylaminoethyl)trimethoxysilane and/or
1-(2-dimethylaminoethyl)silanetriol.

The aforementioned organic silicon compounds of formula (I) are commercially available.
(3-Aminopropyl)trimethoxysilane is available for purchase from Sigma-Aldrich®, for example. (3-Aminopropyl)triethoxysilane is also commercially available from Sigma-Aldrich®.

In a further embodiment, the composition comprises at least one organic silicon compound (a1) of formula (II)

$$(R_5O)_c(R_6)_dSi\text{-}(A)_e\text{-}[NR_7\text{-}(A')]_f\text{—}[O\text{-}(A'')]_g\text{—}[NR_8\text{-}(A''')]_h\text{—}Si(R_6')_{d'}(OR_5')_{c'} \quad (II).$$

The organosilicon compounds of formula (II) each bear at their two ends the silicon-containing groupings $(R_5O)_c(R_6)_dSi$— and —$Si(R_6')_{d'}(OR_5')_{c'}$.

In the middle part of the molecule of formula (II) there are the groupings -(A)$_e$- and —[NR$_7$-(A')]$_f$- and —[O-(A'')]$_g$- and —[NR$_8$-(A''')]$_h$- Here, each of the radicals e, f, g and h can independently represent number 0 or 1, with the proviso that at least one of the radicals e, f, g and h is other than 0. In other words, an organic silicon compound of formula (II) contains at least one grouping selected from the group of -(A)- and —[NR$_7$-(A')]- and —[O-(A'')]- and —[NR$_8$-(A''')]-.

In the two terminal structural units $(R_5O)_c(R_6)_dSi$— and —$Si(R_6')_{d'}(OR_5')_{c'}$, the radicals R5, R5', R5'' independently represent a hydrogen atom or a $C_1$-$C_6$ alkyl group. The R6, R6' and R6'' radicals independently represent a $C_1$-$C_6$ alkyl group.

Here, c represents an integer from 1 to 3, and d represents the integer 3-c. If c stands for number 3, then d is 0. If c stands for number 2, then d is equal to 1. If c stands for number 1, then d is equal to 2.

Similarly, c' represents an integer from 1 to 3, and d' represents the integer 3-c'. If c' stands for number 3, then d' is equal to 0. If c' stands for number 2, then d' is equal to 1. If c' stands for number 1, then d' is equal to 2.

Films with the highest stability or dyes with the best wash fastness could be obtained when the radicals c and c' both stand for number 3. In this case, d and d' both stand for number 0.

In another preferred embodiment, a method is exemplified wherein the agent (a) comprises at least one organic silicon compound (a1) of formula (II), $$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{—}Si(R_6')_{d'}(OR_5')_{c'} \quad (II),$$

where
$R_5$ and $R_5'$ independently represent a methyl group or an ethyl group,
c and c' both stand for number 3 and
d and d' both stand for number 0.

When c and c' are both 3 and d and d' are both 0, the organic silicon compounds of the present disclosure correspond to formula (IIa)

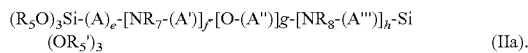
(IIa).

The radicals e, f, g, and h can independently represent number 0 or 1, with at least one radical from e, f, g, and h being different from zero. The abbreviations e, f, g and h thus define which of the groupings -(A)$_e$- and —[NR$_7$—(N)]$_f$— and —[O-(A'')]$_g$- and —[NR$_8$-(A''')]$_h$- are located in the middle part of the organic silicon compound of formula (II).

In this context, the presence of certain groupings has proven to be particularly beneficial in terms of increasing wash fastness. Particularly good results could be obtained if at least two of the radicals e, f, g and h stand for number 1. Very preferably, e and f both stand for number 1. Furthermore, g and h both represent number 0.

When e and f are both 1 and g and h are both 0, the organic silicon compounds as contemplated herein are represented by formula (IIb)

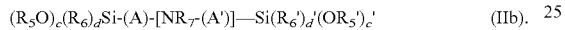
(IIb).

Radicals A, A', A'', A''' and A'''' independently represent a linear or branched C$_1$-C$_{20}$ divalent alkylene group. Preferably, A, A', A'', A''' and A'''' independently represent a linear divalent C$_1$-C$_{20}$ alkylene group. Further preferably, A, A', A'', A''' and A'''' independently represent a linear divalent C$_1$-C$_6$ alkylene group. Particularly preferably, the radicals A, A', A'', A''' and A'''' independently represent a methylene group (—CH$_2$—), an ethylene group (—CH$_2$—CH$_2$—), a propylene group (—CH$_2$—CH$_2$—CH$_2$—) or a butylene group (—CH$_2$—CH$_2$—CH$_2$—CH$_2$—). Very preferably, the radicals A, A', A'', A''' and A'''' represent a propylene group (—CH$_2$—CH$_2$—CH$_2$—).

The divalent C$_1$-C$_{20}$ alkylene group may alternatively be referred to as a divalent or divalent C$_1$-C$_{20}$ alkylene group, by which is meant that each grouping A, A', A'', A''' and A'''' may form two bonds.

The linear propylene group (—CH$_2$—CH$_2$—CH$_2$—) can alternatively be referred to as the propane-1,3-diyl group.

When the radical f represents number 1, the organic silicon compound of formula (II) contains a structural grouping —[NR$_7$-(A)]-.

When the radical h represents number 1, the organic silicon compound of formula (II) contains a structural grouping —[NR$_8$-(A'')]-.

Wherein R$_7$ and R$_8$ independently represent a hydrogen atom, a C$_1$-C$_6$ alkyl group, a hydroxy-C$_1$-C$_6$ alkyl group, a C$_2$-C$_6$ alkenyl group, an amino-C$_1$-C$_6$ alkyl group or a group of formula (III)

(III).

Very preferably, R$_7$ and R$_8$ independently represent a hydrogen atom, a methyl group, a 2-hydroxyethyl group, a 2-alkenyl group, a 2-aminoethyl group or a group of formula (III).

When the radical f represents number 1 and the radical h represents number 0, the organic silicon compound contains the grouping [NR$_7$-(A')] but not the grouping —[NR$_8$-(A'')]. If the radical R7 now stands for a grouping of the formula (III), the agent (a) contains an organic silicon compound with 3 reactive silane groups.

In another preferred embodiment, a method is exemplified in that the agent (a) comprises at least one organic silicon compound (a1) of formula (II),

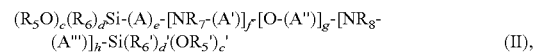
(II), where e and f both stand for the number 1, g and h both stand for the number 0, A and A' independently of one another represent a linear, divalent C$_1$-C$_6$ alkylene group and R$_7$ represents a hydrogen atom, a methyl group, a 2-hydroxyethyl group, a 2-alkenyl group, a 2-aminoethyl group or a group of formula (III).

In a further preferred embodiment, a method is exemplified in that the agent (a) comprises at least one organic silicon compound of formula (II), wherein e and f both stand for the number 1, g and h both stand for the number 0, A and A' independently represent a methylene group (—CH$_2$—), an ethylene group (—CH$_2$—CH$_2$—) or a propylene group (—CH$_2$—CH$_2$—CH$_2$—), and R$_7$ represents a hydrogen atom, a methyl group, a 2-hydroxyethyl group, a 2-alkenyl group, a 2-aminoethyl group or a group of formula (III).

Organic silicon compounds of formula (II) which are well suited for solving the problem as contemplated herein are

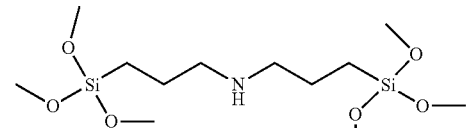

-3-(Trimethoxysilyl)-N-[3-(trimethoxysilyl)propyl]-1-propanamine

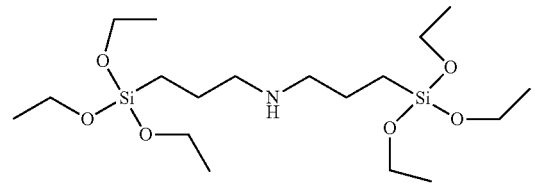

-3-(Triethoxysilyl)-N-[3-triethoxysilyl)propyl]-1-propanamine

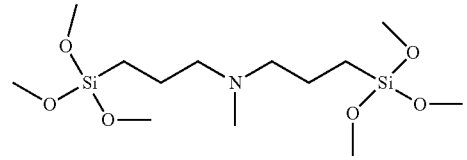

-N-methyl-3-(trimethoxysilyl)-N-[3-(trimethoxysilyl)propyl]-1-propanamine

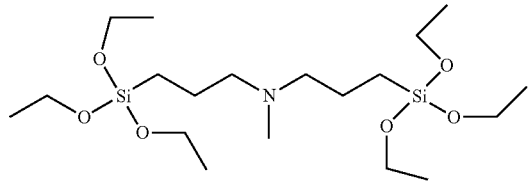

-N-methyl-3-(triethoxysilyl)-N-[3-(triethoxysilyl)propyl]-1-propanamine

-continued

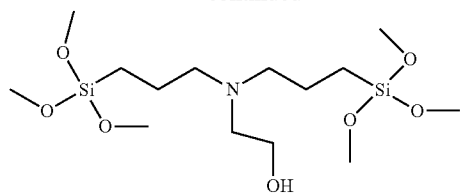
-2-Bis[3-(trimethoxysilyl)propyl]amino]ethanol

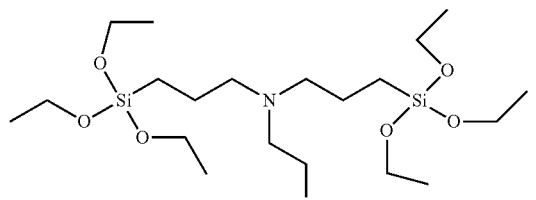
-2-[Bis[3-(triethoxysilyl)propyl]amino]ethanol

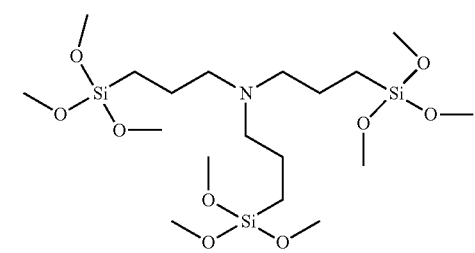
-3-(Trimethoxysilyl)-N,N-bis[3-(trimethoxysilyl)propyl]-1-propanamine

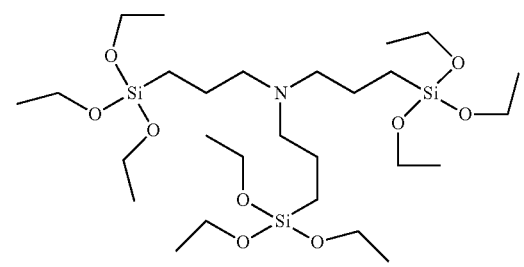
- 3-(Triethoxysilyl)-N,N-bis[3-(triethoxysilyl)propyl]-1-propanamine

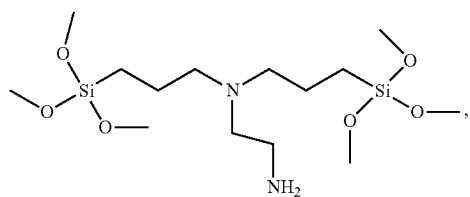
- N1,N1-bis[3(trimethoxysilyl)propyl]-1,2-ethanediamine

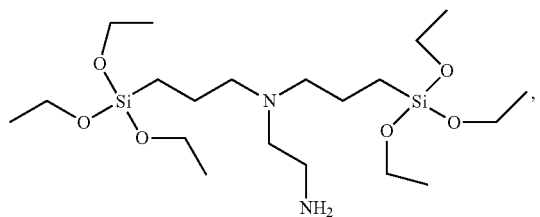
-N1,N1-bis[3-(triethoxysilyl)propyl]-1,2-ethanediamine

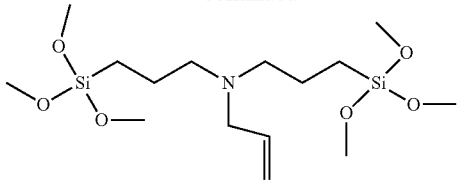
-N1,N1-bis[3-(trimethoxysilyl)propyl]-2-propen-1-amine

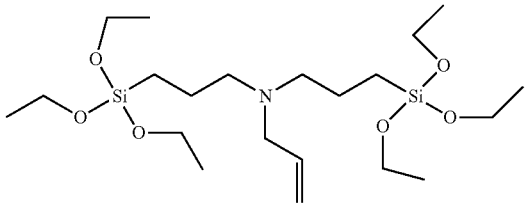
-N,N-bis[3-(triethoxysilyl)propyl]-2-propen-1-amine

The aforementioned organic silicon compounds of formula (II) are commercially available.
Bis(trimethoxysilylpropyl)amines with CAS number 82985-35-1 can be purchased from Sigma-Aldrich®, for example.
Bis[3-(triethoxysilyl)propyl]amines with CAS number 13497-18-2 can be purchased from Sigma-Aldrich®, for example.
N-methyl-3-(trimethoxysilyl)-N-[3-(trimethoxysilyl)propyl]-1-propanamine is alternatively known as bis(3-trimethoxysilylpropyl)-N-methylamine and can be purchased commercially from Sigma-Aldrich® or Fluorochem®.
3-(Triethoxysilyl)-N,N-bis[3-(triethoxysilyl)propyl]-1-propanamine with CAS number 18784-74-2 can be purchased from Fluorochem® or Sigma-Aldrich®, for example.
In a further preferred embodiment, a method is exemplified in that the agent (a) comprises at least one organic silicon compound (a1) selected from the group of:
3-(Trimethoxysilyl)-N-[3-(trimethoxysilyl)propyl]-1-propanamine
3-(Triethoxysilyl)-N-[3-(triethoxysilyl)propyl]-1-propanamine
N-methyl-3-(trimethoxysilyl)-N-[3-(trimethoxysilyl)propyl]-1-propanamine
N-methyl-3-(triethoxysilyl)-N-[3-(triethoxysilyl)propyl]-1-propanamine
2-[Bis[3-(trimethoxysilyl)propyl]amino]ethanol
2-[Bis[3-(triethoxysilyl)propyl]amino]ethanol
3-(Trimethoxysilyl)-N,N-bis[3-(trimethoxysilyl)propyl]-1-propanamine
3-(triethoxysilyl)-N,N-bis[3-(triethoxysilyl)propyl]-1-propanamine
N1,N1-bis[3-(trimethoxysilyl)propyl]-1,2-ethanediamine,
N1,N1-bis[3-(triethoxysilyl)propyl]-1,2-ethanediamine,
N,N-bis[3-(trimethoxysilyl)propyl]-2-propen-1-amine and/or
N,N-bis[3-(triethoxysilyl)propyl]-2-propen-1-amine.

In further tests, in particular dyeing tests, it has also been found to be particularly advantageous if the agent (a) applied to the keratinous material in the process contains at least one organic silicon compound of the formula (IV)

$$R_9Si(OR_{10})_k(R_{11})_m \qquad (IV).$$

The compounds of formula (IV) are organic silicon compounds selected from silanes having one, two or three silicon atoms, wherein the organic silicon compound comprises one or more hydroxyl groups and/or hydrolyzable groups per molecule.

The organic silicon compound(s) of formula (IV) may also be referred to as silanes of the alkyl-alkoxy-silane or alkyl-hydroxy-silane type, $$R_9Si(OR_{10})_k(R_{11})_m \quad (IV),$$

where
- $R_9$ stands for a $C_1$-$C_{18}$ alkyl group,
- $R_{10}$ represents a hydrogen atom or a $C_1$-$C_6$ alkyl group,
- $R_{11}$ stands for a $C_1$-$C_6$ alkyl group
- k is an integer from 1 to 3, and
- m stands for the integer 3-k.

In a further preferred embodiment, the method is exemplified in that the agent (a) comprises at least one organic silicon compound (a1) of formula (IV)

$$R_9Si(OR_{10})_k(R_{11})_m \quad (IV),$$

where
- $R_9$ stands for a $C_1$-$C_{18}$ alkyl group,
- $R_{10}$ represents a hydrogen atom or a $C_1$-$C_6$ alkyl group,
- $R_{11}$ stands for a $C_1$-$C_6$ alkyl group
- k is an integer from 1 to 3, and
- m stands for the integer 3-k.

In a further preferred embodiment, a process is exemplified in that the agent (a) comprises, in addition to the organic silicon compound or compounds of formula (I), at least one further organic silicon compound of formula (IV)

$$R_9Si(OR_{10})_k(R_{11})_m \quad (IV),$$

where
- $R_9$ stands for a $C_1$-$C_{18}$ alkyl group,
- $R_{10}$ represents a hydrogen atom or a $C_1$-$C_6$ alkyl group,
- $R_{11}$ stands for a $C_1$-$C_6$ alkyl group
- k is an integer from 1 to 3, and
- m stands for the integer 3-k.

In a further preferred embodiment, a process is exemplified in that the agent (a) comprises, in addition to the organic silicon compound or compounds of formula (II), at least one further organic silicon compound of formula (IV)

$$R_9Si(OR_{10})_k(R_{11})_m \quad (IV),$$

where
- $R_9$ stands for a $C_1$-$C_{18}$ alkyl group,
- $R_{10}$ represents a hydrogen atom or a $C_1$-$C_6$ alkyl group,
- $R_{11}$ stands for a $C_1$-$C_6$ alkyl group
- k is an integer from 1 to 3, and
- m stands for the integer 3-k.

In a further preferred embodiment, a process is exemplified in that the agent (a) comprises, in addition to the organic silicon compound or compounds of formula (I) and/or (II), at least one further organic silicon compound of formula (IV)

$$R_9Si(OR_{10})_k(R_{11})_m \quad (IV),$$

where
- $R_9$ stands for a $C_1$-$C_{18}$ alkyl group,
- $R_{10}$ represents a hydrogen atom or a $C_1$-$C_6$ alkyl group,
- $R_{11}$ stands for a $C_1$-$C_6$ alkyl group
- k is an integer from 1 to 3, and
- m stands for the integer 3-k.

In the organic silicon compounds of formula (IV), the $R_9$ radical represents a $C_1$-$C_{18}$ alkyl group. This $C_1$-$C_{18}$ alkyl group is saturated and can be linear or branched. Preferably, $R_9$ represents a linear $C_1$-$C_{18}$ alkyl group. Preferably, $R_9$ represents a methyl group, an ethyl group, an n-propyl group, an n-butyl group, an n-pentyl group, an n-hexyl group, an n-octyl group, an n-dodecyl group or an n-octadecyl group. Particularly preferably, $R_9$ represents a methyl group, an ethyl group, an n-hexyl group or an n-octyl group.

In the organic silicon compounds of form (IV), the $R_{10}$ radical represents a hydrogen atom or a $C_1$-$C_6$ alkyl group. Particularly preferably, $R_{10}$ represents a methyl group or an ethyl group.

In the organic silicon compounds of form (IV), the $R_{11}$ radical represents a $C_1$-$C_6$ alkyl group. Particularly preferably, $R_{11}$ represents a methyl group or an ethyl group.

Furthermore, k stands for an integer from 1 to 3, and m stands for the integer 3-k. If k stands for number 3, then m is 0. If k stands for number 2, then m is equal to 1. If k stands for number 1, then m is equal to 2.

Particularly stable films, i.e. dyeings with particularly good wash fastness properties, could be obtained if an agent (a) containing at least one organic silicon compound (a1) corresponding to formula (IV): in which the radical k is number 3, was used in the process. In this case, the remainder m stands for number 0.

Organic silicon compounds of the formula (IV) which are particularly suitable for solving the problem as contemplated herein are

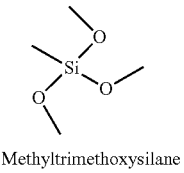

-Methyltrimethoxysilane

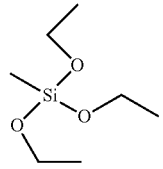

-Methyltriethoxysilane

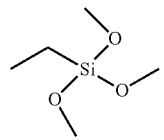

-Ethyltrimethoxysilane

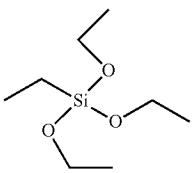

-Ethyltriethoxysilane

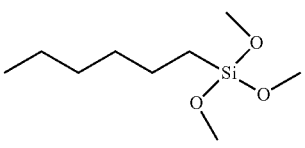

-n-Hexyltrimethoxysilane

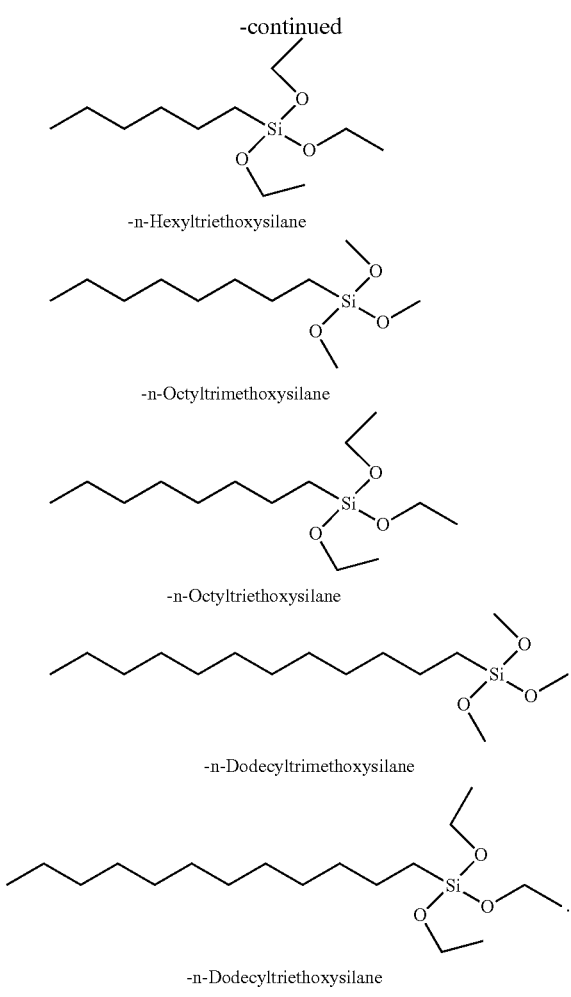

-n-Hexyltriethoxysilane

-n-Octyltrimethoxysilane

-n-Octyltriethoxysilane

-n-Dodecyltrimethoxysilane

-n-Dodecyltriethoxysilane and octadecyltrimethoxysilane and/or octadecyltriethoxysilane In another preferred embodiment, a method is exemplified in that the agent (a) comprises at least one organic silicon compound (a1) of formula (IV) selected from the group of:
Methyltrimethoxysilane
Methyltriethoxysilane
Ethyltrimethoxysilane
Ethyltriethoxysilane
Propyltrimethoxysilane
Propyltriethoxysilane
Hexyltrimethoxysilane
Hexyltriethoxysilane
Octyltrimethoxysilane
Octyltriethoxysilane
Dodecyltrimethoxysilane
Dodecyltriethoxysilane
Octadecyltrimethoxysilane and/or
Octadecyltriethoxysilane.

The organic silicon compounds described above are reactive compounds. In this context, it has been found preferable if the agent (a)—based on the total weight of the agent (a)—contains one or more organic silicon compounds (a1) in a total amount of about 0.1 to about 20% by weight, preferably about 1 to about 15% by weight and particularly preferably about 2 to about 8% by weight.

In a further preferred embodiment, a process is exemplified in that the agent (a) contains—based on the total weight of the agent (a)—one or more organic silicon compounds (a1) in a total amount of about 0.1 to about 20% by weight, preferably about 1 to about 15% by weight and particularly preferably about 2 to about 8% by weight.

To achieve particularly good dyeing results, it is particularly advantageous to use the organic silicon compounds of formula (I) and/or (II) in certain ranges of amounts in the agent (a). Particularly preferably, the agent (a) contains—based on the total weight of the agent (a)—one or more organic silicon compounds of the formula (I) and/or (II) in a total amount of about 0.1 to about 10% by weight, preferably about 0.5 to about 5% by weight and particularly preferably about 0.5 to about 3% by weight.

In a further preferred embodiment, a process is exemplified in that the agent (a) contains—based on the total weight of the agent (a)—one or more organic silicon compounds of the formula (I) and/or (II) in a total amount of about 0.1 to about 10% by weight, preferably about 0.5 to about 5% by weight and particularly preferably about 0.5 to about 3% by weight.

Furthermore, it has been found to be particularly preferred if the organic silicon compound(s) of formula (IV) is/are also present in the agent (a) in certain ranges of amounts. Particularly preferably, the agent (a) contains—based on the total weight of the agent (a)—one or more organic silicon compounds of the formula (IV) in a total amount of about 0.1 to about 20% by weight, preferably about 2 to about 15% by weight and particularly preferably about 4 to about 9% by weight.

In a further preferred embodiment, a process is exemplified in that the agent (a) contains—based on the total weight of the agent (a)—one or more organic silicon compounds of the formula (IV) in a total amount of about 0.1 to about 20% by weight, preferably about 2 to about 15% by weight and particularly preferably about 3.2 to about 10% by weight.

In the course of the work leading to this present disclosure, it was found that particularly stable and uniform films could be obtained on the keratinous material even when the agent (a) contained two organic silicon compounds that were structurally different from each other.

In another preferred embodiment, a method is exemplified in that the agent (a) comprises at least two structurally different organic silicon compounds.

In a preferred embodiment, a process is exemplified in that an agent (a) comprising at least one organic silicon compound of formula (I) and at least one organic silicon compound of formula (IV) is applied to the keratinous material.

In an explicitly very particularly preferred embodiment, a process is exemplified in that there is applied to the keratinous material an agent (a) comprising at least one organic silicon compound of formula (I) selected from the group of (3-aminopropyl)triethoxysilane and (3-aminopropyl)trimethoxysilane and additionally containing at least one organic silicon compound of formula (IV) selected from the group of methyltrimethoxysilane, methyltriethoxysilane, ethyltrimethoxysilane, ethyltriethoxysilane, propyltrimethoxysilane, propyltriethoxysilane, hexyltrimethoxysilane and hexyltriethoxysilane.

In a further preferred embodiment, a method is exemplified in that the agent (a) comprises—based on the total weight of the agent (a):
about 0.5 to about 5% by weight % of at least one first organic silicon compound (a1) which is selected from the group of (3-aminopropyl)trimethoxysilane, (3-aminopropyl)triethoxysilane, (2-aminoethyl)trimethoxysilane, (2-aminoethyl)triethoxysilane, (3-dimethylaminopropyl)trimethoxysilane, (3-dimethylaminopropyl)

triethoxysilane (2-dimethylaminoethyl) trimethoxysilane and (2-dimethylaminoethyl) triethoxysilane, and about 3.2 to about 10 wt % of at least one second organic silicon compound (a1) selected from the group of methyltrimethoxysilane, methyltriethoxysilane, ethyltrimethoxysilane, ethyltriethoxysilane, propyltrimethoxysilane, Propyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane and octadecyltriethoxysilane.

In this embodiment, the agent (a) comprises one or more organic silicon compounds of a first group in a total amount of about 0.5 to about 3% by weight. The organic silicon compounds of this first group are selected from the group of (3-aminopropyl)trimethoxysilane, (3-aminopropyl)triethoxysilane, (2-aminoethyl)trimethoxysilane, (2-aminoethyl)triethoxysilane, (3-dimethylaminopropyl)trimethoxysilane, (3-dimethylaminopropyl)triethoxysilane (2-dimethylaminoethyl)trimethoxysilane and/or (2-dimethyl aminoethyl)triethoxysane.

In this embodiment, the agent (a) comprises one or more organic silicon compounds of a second group in a total amount of about 3.2 to about 10 wt %. The organic silicon compounds of this second group are selected from the group of methyltrimethoxysilane, methyltriethoxysilane, ethyltrimethoxysilane, ethyltriethoxysilane, propyltrimethoxysilane, Propyltriethoxysilane, hexyltrimethoxysilane, hexyltriethoxysilane, octyltrimethoxysilane, octyltriethoxysilane, dodecyltrimethoxysilane, dodecyltriethoxysilane, octadecyltrimethoxysilane and octadecyltriethoxysilane.

Even the addition of small amounts of water leads to hydrolysis in organic silicon compounds with at least one hydrolyzable group. The hydrolysis products and/or organic silicon compounds having at least one hydroxy group may react with each other in a condensation reaction. For this reason, both the organosilicon compounds having at least one hydrolyzable group and their hydrolysis and/or condensation products may be present in the agent (a). When organosilicon compounds having at least one hydroxyl group are used, both the organic silicon compounds having at least one hydroxyl group and their condensation products may be present in the agent (a).

A condensation product is understood to be a product formed by the reaction of at least two organic silicon compounds each having at least one hydroxyl group or hydrolyzable group per molecule with elimination of water and/or with elimination of an alkanol. The condensation products can be, for example, dimers, but also trimers or oligomers, with the condensation products being in equilibrium with the monomers. Depending on the amount of water used or consumed in the hydrolysis, the equilibrium shifts from monomeric organic silicon compounds to condensation product.

Particularly good results were obtained when organic silicon compounds of formula (I) and/or (II) were used in the process. Since, as already described above, hydrolysis/condensation already starts at traces of moisture, the hydrolysis and/or condensation products of the organic silicon compounds (I) and/or (II) are also included in this embodiment.

Hydroxycarboxylic acid esters (a2)

When agent (a) is applied to the keratinous material, the organic silicon compound(s) (a1), which preferably comprise one or more hydroxyl groups or hydrolyzable groups per molecule, are first hydrolyzed and oligomerized or polymerized in the presence of water. The hydrolysis products or oligomers formed in this way have a particularly high affinity for the surface of the keratinous material. If hydroxycarboxylic acid esters (a2) are simultaneously present in the agent (a), they are integrated into the resulting oligomers or polymers. If the agent (a) further comprises at least one colorant compound, the film formed on the keratinous material is a colored film. Following the application of agent (a), agent (b) is now applied, whereby the sealing reagent contained in this agent (b) seals the, possibly colored, film. If the agent (b) further contains at least one colorant compound, either the uncolored film produced in the first step is sealed and colored, or the color impression of the colored film produced in the first step is enhanced or modified, depending on the colorant compound used, or the color impression of the first film is enhanced or modified by forming a second, colored film on the first, colored film. If the agent (b) does not contain a colorant compound, the colored film prepared in the first step is sealed. Successive application of agents (a) and (b) produces a coloration that is particularly resistant to external influences.

As an ingredient (a2) essential to the present disclosure, the agent (a) used in the dyeing process contains at least one hydroxycarboxylic acid ester.

It has been shown that hydroxycarboxylic acid esters have adhesion-promoting properties with respect to the at least one colorant compound and that particularly stable colorations can thus be obtained.

Hydroxycarboxylic acids are carboxylic acids that have both at least one carboxy group and one or more hydroxy group(s). Hydroxycarboxylic acids represent widespread organic substances in nature.

Suitable hydroxycarboxylic acids include, for example, α-hydroxy carboxylic acids and/or β-hydroxycarboxylic acids. Particularly suitable hydroxycarboxylic acids are selected from the group of citric acid, malic acid, tartaric acid, lactic acid, gluconic acid, glycolic acid, tartronic acid, mandelic acid, salicylic acid, glyceric acid and mixtures thereof. Particularly preferred is the hydroxycarboxylic acid selected from the group of citric acid, malic acid, tartaric acid, lactic acid and mixtures thereof. The hydroxycarboxylic acid citric acid is particularly preferred.

Accordingly, in a preferred embodiment, the process is exemplified in that the agent (a) comprises at least one hydroxycarboxylic acid ester (a2) selected from the group of citric acid esters, malic acid esters, tartaric acid esters, lactic acid esters, gluconic acid esters, glycolic acid esters, tartronic acid esters, mandelic acid esters, salicylic acid esters, glyceric acid esters and mixtures thereof.

In a more preferred embodiment, the process is exemplified in that the agent (a) comprises at least one hydroxycarboxylic acid ester (a2) selected from the group of citric acid esters, malic acid esters, tartaric acid esters, lactic acid esters and mixtures thereof.

In a highly preferred embodiment, the method is exemplified in that the agent (a) comprises at least one hydroxycarboxylic acid ester (a2) selected from the group of citric acid esters.

Hydroxycarboxylic acid esters are the esters of hydroxycarboxylic acids with aliphatic alcohols. The aliphatic alcohols are in particular linear or branched, saturated or unsaturated alcohols with 1 to about 22 carbon atoms and 0, 1, 2 or 3 double bonds. Typical representatives are, for example, methanol, ethanol, n-propanol, isopropanol, n-butanol, sec-butanol, tert-butanol, n-pentanol, capric caprylic alcohol, 2-ethylhexanol, capric alcohol, myristyl alcohol, lauryl alcohol, cetyl alcohol, palmitoleyl alcohol, stearyl alcohol, oleyl alcohol, elaidyl alcohol, petroselyl alcohol, linolyl alcohol, linolenyl alcohol, behenyl alcohol or erucyl alcohol. Preferably, the aliphatic alcohols are linear or branched, saturated alcohols having 1 to 6 carbon atoms, which are preferably selected from the group of ethanol, n-propanol, isopropanol, n-butanol, sec-butanol tert-butanol and mixtures thereof. Very preferably, the aliphatic alcohol is ethanol.

Accordingly, in a preferred embodiment, the method is exemplified in that the agent (a) comprises at least one hydroxycarboxylic acid ester (a2) selected from the group of citric acid triethyl ester (triethyl citrate), malic acid diethyl ester (diethyl malate), tartaric acid diethyl ester (diethyl tartrate), lactic acid ethyl ester (ethyl lactate) and mixtures thereof in a preferred embodiment, the process exemplified in that the agent (a) contains at least one hydroxycarboxylic acid ester (a2) comprising citric acid triethyl ester.

Particularly good results were obtained when the agent (a)—based on the total weight of the agent (a)—contains one or more hydroxycarboxylic acid esters (a2) in a total amount of from about 1 to about 50% by weight, preferably from about 5 to about 35% by weight and very preferably from about 10 to about 25% by weight.

Diol (a3)

As an essential component (a3) of the present disclosure, the agent (a) used in the dyeing process contains at least one diol.

A diol is a chemical compound with two hydroxyl groups (—OH groups). An aliphatic diol is also known as a glycol.

Preferred diols are $C_2$-$C_9$ alkanols with two hydroxyl groups and polyethylene glycols with 3 to about 20 ethylene oxide units. The agents (a) comprise at least one $C_2$-$C_9$ alkanol having two hydroxyl groups or at least one water-soluble polyethylene glycol having 3 to about 20 ethylene oxide units or mixtures of at least one $C_2$-$C_9$ alkanol having two hydroxyl groups and at least one water-soluble polyethylene glycol having 3 to about 20 ethylene oxide units.

Preferably, the $C_2$-$C_9$ alkanols with two hydroxyl groups are selected from ethylene glycol, 1,2-propylene glycol, 1,3-propylene glycol, 2-methyl-1,3-propanediol, 1,2-butylene glycol, 1,3-butylene glycol, 1,4-butylene glycol, 1,2-pentanediol, 1,5-pentanediol, 1,2-hexanediol, 1,6-hexanediol, 1,2-octanediol, 1,8-octanediol, cis-1,4-dimethylolcyclohexane, trans-1,4-dimethylolcyclohexane, any isomeric mixtures of cis- and trans-1,4-dimethylolcyclohexane, and mixtures of these diols. Also suitable diols are diethylene glycol, dipropylene glycol and/or PPG-10 butanediol (INCI). Suitable water-soluble polyethylene glycols are selected from PEG-3, PEG-4, PEG-6, PEG-7, PEG-8, PEG-9, PEG-10, PEG-12, PEG-14, PEG-16, PEG-18 and PEG-20, and mixtures thereof.

Of said diols, the agent (a) preferably contains at least one diol selected from the group of ethylene glycol, 1,2-propylene glycol, 1,3-propylene glycol, 1,2-butylene glycol, 1,3-butylene glycol, 1,4-butylene glycol, 1,2-pentanediol, 1,5-pentanediol, 1,2-hexanediol, 1,6-hexanediol, PEG-8, PEG-32 and PPG-10 butanediol (INCI).

In a highly preferred embodiment, the method is exemplified in that the agent (a) comprises at least one diol (a3) selected from the group of ethylene glycol, 1,2-propylene glycol and 1,3-propylene glycol.

Particularly good results were obtained when the agent (a)—based on the total weight of the agent (a)—contains one or more diols (a3) in a total amount of from about 1 to about 50% by weight, preferably from about 2 to about 35% by weight and very preferably from about 5 to about 25% by weight.

pH Value of the Agent (a)

It has been found to be preferable if the agent (a) is prepared in the form of a water-containing agent, i.e. the water content of the agent is greater than or equal to about 5% by weight, based on the total amount of agent (a), which is adjusted to an alkaline ph.

To adjust the pH, the agent (a) may contain at least one alkalizing agent.

To adjust the desired pH, the agents (a) may therefore also contain at least one alkalizing agent. The pH values for the purposes of the present disclosure are pH values measured at a temperature of 22° C.

As alkalizing agent, agent (a) may contain, for example, ammonia, alkanolamines and/or basic amino acids.

The alkanolamines that can be used in the composition are preferably selected from primary amines having a $C_2$-$C_6$ alkyl parent carrying at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol.

Particularly preferred alkanolamines are selected from 2-aminoethan-1-ol and/or 2-amino-2-methylpropan-1-ol. A particularly preferred embodiment is therefore exemplified in that the agent contains, as alkalizing agent, an alkanolamine selected from 2-aminoethan-1-ol and/or 2-amino-2-methylpropan-1-ol.

For the purposes of the present disclosure, an amino acid is an organic compound containing in its structure at least one protonatable amino group and at least one —COOH or one —$SO_3H$ group. Preferred amino acids are aminocarboxylic acids, in particular α-(alpha)-aminocarboxylic acids and w-aminocarboxylic acids, with α-aminocarboxylic acids being particularly preferred.

Basic amino acids are those amino acids which have an isoelectric point pI greater than about 7.

Basic α-aminocarboxylic acids contain at least one asymmetric carbon atom. In the context of the present disclosure, both possible enantiomers can be used equally as specific compounds or also mixtures thereof, in particular as racemates. However, it is particularly advantageous to use the naturally preferable isomeric form, usually in L-configuration.

The basic amino acids are preferably selected from the group formed by arginine, lysine, ornithine and histidine, particularly preferably arginine and lysine. In a further particularly preferred embodiment, an agent is therefore exemplified in that the alkalizing agent is a basic amino acid selected from the group of arginine, lysine, ornithine and/or histidine.

In addition, the agent may contain further alkalizing agents, in particular inorganic alkalizing agents. Inorganic alkalizing agents that can be used as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Very particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Although the agents (a) are preferably adjusted to pH values in the alkaline range, it may nevertheless be necessary in principle to also use acidifiers in small quantities for fine adjustment of the desired pH value. Acidifiers suitable as contemplated herein are, for example, citric acid, lactic acid, acetic acid or also dilute mineral acids (such as hydrochloric acid, sulfuric acid, phosphoric acid).

However, in the course of the work leading to the present disclosure, it has been found that the presence of the alkalizing agent or the adjustment of the alkaline pH is essential for the formation of resistant films on the keratinous material. The presence of excessive amounts of acids can have a negative effect on the strength of the films. For this reason, it has proved preferable to keep the quantities of acids used in the agent (a) as low as possible. For this reason, it is advantageous if the total amount of organic and/or inorganic acids contained in the agent (a) does not exceed a certain value.

In a further preferred embodiment, a process is exemplified in that the total amount of organic acids from the group of citric acid, tartaric acid, malic acid and lactic acid contained in the agent (a) is below about 1% by weight, preferably below about 0.7% by weight, more preferably below about 0.5% by weight, even more preferably below about 0.1% by weight and most preferably below about 0.01% by weight.

In a further preferred embodiment, a process is exemplified in that the total amount of inorganic acids from the group comprising hydrochloric acid, sulfuric acid and phosphoric acid contained in the agent (a) is below about 1% by weight, preferably below about 0.7% by weight, more preferably below about 0.5% by weight, still more preferably below about 0.1% by weight and very particularly preferably below about 0.01% by weight.

The maximum total amounts of the acids contained in the agent (a) given above are always based on the total weight of the agent (a).

Agent (b)

The method of treatment of keratinous material includes, in addition to the application of agent (a), the application of agent (b). The agent (b) is exemplified in that it contains at least one sealing reagent (b1).

Agent (b) is a post-treatment agent and the application of agent (b) to the keratinous material treated with agent (a) has the effect of making the colorations obtained in the process more durable. In particular, the use of agent (b) can improve the fastness to washing and the fastness to rubbing of the dyeings obtained in the process.

It is preferred that the sealing reagent comprises a compound selected from the group of film forming polymers, alkalizing agents, acidifying agents, and mixtures thereof.

It may be preferred that the sealing reagent comprises a film-forming polymer.

Polymers are understood to be macromolecules with a molecular weight of at least about 1000 g/mol, preferably of at least about 2500 g/mol, particularly preferably of at least about 5000 g/mol, which consist of identical, repeating organic units. The polymers of the present disclosure may be synthetically produced polymers prepared by polymerizing one type of monomer or by polymerizing different types of monomers that are structurally different from each other. If the polymer is produced by polymerization of a monomer type, it is referred to as homo-polymers. If structurally different monomer types are used in the polymerization, the resulting polymer is called a copolymer.

The maximum molecular weight of the polymer depends on the degree of polymerization (number of polymerized monomers) and the batch size, and is partly determined by the polymerization method. In terms of the present disclosure, it is preferred if the maximum molecular weight of the film-forming polymer as sealing reagent (b1) is not more than about $10^7$ g/mol, preferably not more than about $10^6$ g/mol, and particularly preferably not more than about $10^5$ g/mol.

For the purposes of the present disclosure, a film-forming polymer is understood to be a polymer capable of forming a film on a substrate, for example on a keratinous material or a keratinous fiber. The formation of a film can be demonstrated, for example, by viewing the polymer-treated keratinous material under a microscope.

The film-forming polymers (b1) in the agent (b) can be hydrophilic or hydrophobic.

In a first embodiment, it may be preferred to use at least one hydrophobic film-forming polymer in agent (b).

A hydrophobic polymer is defined as a polymer that has a solubility in water at 25° C. (760 mmHg) of less than 1% by weight.

For example, the water solubility of the film-forming hydrophobic polymer can be determined in the following way. 1 g of the polymer is placed in a beaker. Water is added to make up to 100 g. A stirring rod is added and the mixture is heated to 25° C. on a magnetic stirrer with stirring. It is stirred for 60 minutes. The aqueous mixture is then visually assessed. If the polymer-water mixture cannot be visually assessed due to high turbidity of the mixture, the mixture is filtered. If a portion of undissolved polymer remains on the filter paper, then the solubility of the polymer is less than 1% by weight.

In particular, the polymers of the acrylic acid type, the polyurethanes, the polyesters, the polyamides, the polyureas, the cellulose polymers, the nitrocellulose polymers, the silicone polymers, the polymers of the acrylamide type and the polyisoprenes can be mentioned here.

Particularly suitable film-forming, hydrophobic polymers are, for example, polymers from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

In a further preferred embodiment, a composition (b) is exemplified in that it comprises at least one film-forming, hydrophobic polymer (b1) selected from the group of the copolymers of acrylic acid, the copolymers of methacrylic acid, the homopolymers or copolymers of acrylic acid esters, the homopolymers or copolymers of methacrylic acid esters homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Film-forming hydrophobic polymers selected from the group of synthetic polymers, polymers obtainable by free-radical polymerization or natural polymers have proved particularly suitable for solving the problem as contemplated herein.

Other particularly well-suited film-forming hydrophobic polymers can be selected from the homopolymers or copolymers of olefins, such as cycloolefins, butadiene, isoprene or styrene, vinyl ethers, vinyl amides, the esters or amides of (meth)acrylic acid having at least one $C_1$-$C_{20}$ alkyl group, an aryl group or a $C_2$-$C_{10}$ hydroxyalkyl group.

Other film-forming hydrophobic polymers may be selected from the homo- or copolymers of isooctyl (meth)acrylate, isononyl (meth)acrylate, 2-ethylhexyl (meth)acrylate, lauryl (meth)acrylate), isopentyl (meth)acrylate, n-butyl (meth)acrylate), Isobutyl (meth)acrylate, ethyl (meth)acrylate, methyl (meth)acrylate, tert-butyl (meth)acrylate, stearyl (meth)acrylate, hydroxyethyl (meth)acrylate, 2-hydroxypropyl (meth)acrylate, 3-hydroxypropyl (meth)acrylate and/or mixtures thereof.

Further film-forming hydrophobic polymers can be selected from the homo- or copolymers of (meth)acrylamide, N-alkyl(meth)acrylamides, in particular those with $C_2$-$C_{18}$ alkyl groups, such as N-ethyl acrylamide, N-tert-butylacrylamide, le N-octylacrylamide, N-di($C_1$-$C_4$)alkyl (meth)acrylamide.

Other preferred anionic copolymers are, for example, copolymers of acrylic acid, methacrylic acid or their $C_1$-$C_6$ alkyl esters, as sold under the INCI declaration Acrylates Copolymers. A suitable commercial product is, for example, Aculyn® 33 from Rohm & Haas. However, copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are in particular acrylic acid, methacrylic acid and itaconic acid; suitable alkoxylated fatty alcohols are in particular steareth-20 or ceteth-20.

Very particularly preferred polymers on the market are, for example, Aculyn® 22 (Acrylates/Steareth-20 Methacrylate Copolymer), Aculyn® 28 (Acrylates/Beheneth-25 Methacrylate Copolymer), Structure 2001® (Acrylates/Steareth-20 Itaconate Copolymer), Structure 3001® (Acrylates/Ceteth-20 Itaconate Copolymer), Structure Plus® (Acrylates/Aminoacrylates $C_{10}$-30 Alkyl PEG-20 Itaconate Copolymer), Carbopol® 1342, 1382, Ultrez 20, Ultrez 21 (Acrylates/$C_{10}$-30 Alkyl Acrylate Crosspolymer), Synthalen W 2000® (Acrylates/Palmeth-25 Acrylate Copolymer) or the Rohme and Haas distributed Soltex® OPT (Acrylates/$C_{12}$-22 Alkyl methacrylate Copolymer).

Suitable polymers based on vinyl monomers may include, for example, the homopolymers and copolymers of N-vinylpyrrolidone, vinylcaprolactam, vinyl-($C_1$-$C_6$)alkyl-pyrrole, vinyl oxazole, vinyl thiazole, vinyl pyrimidine or vinyl imidazole.

Also particularly suitable are the copolymers octylacrylamide/acrylates/butylaminoethyl methacrylate copolymer, such as those sold commercially by NATIONAL STARCH under the trade names AMPHOMER® or LOVOCRYL® 47, or the copolymers of acrylates/octylacrylamides sold under the trade names DERMACRYL® LT and DERMACRYL® 79 by NATIONAL STARCH.

Suitable polymers based on olefins include, for example, the homopolymers and copolymers of ethylene, propylene, butene, isoprene and butadiene.

In another embodiment, the film-forming hydrophobic polymers may be the block copolymers comprising at least one block of styrene or the derivatives of styrene. These block copolymers may be copolymers containing one or more blocks in addition to a styrene block, such as styrene/ethylene, styrene/ethylene/butylene, styrene/butylene, styrene/isoprene, styrene/butadiene. Corresponding polymers are sold commercially by BASF® under the trade name "Luvitol® HSB".

Surprisingly, it was found that particularly intense and washfast colorations could be obtained when agent (b) contained at least one film-forming polymer as sealing reagent (b1), which was selected from the group of homopolymers and copolymers of acrylic acid, homopolymers and copolymers of methacrylic acid, homopolymers and copolymers of acrylic acid esters, homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further preferred embodiment, a process is exemplified in that the agent (b) comprises at least one film-forming polymer as sealing agent (b1), which is selected from the group of the homopolymers and copolymers of acrylic acid, the homopolymers and copolymers of methacrylic acid, the homopolymers and copolymers of acrylic acid esters, the homopolymers and copolymers of methacrylic acid esters, homopolymers and copolymers of acrylic acid amides, homopolymers and copolymers of methacrylic acid amides, homopolymers and copolymers of vinylpyrrolidone, homopolymers and copolymers of vinyl alcohol, homopolymers and copolymers of vinyl acetate, homopolymers and copolymers of ethylene, homopolymers and copolymers of propylene, homopolymers and copolymers of styrene, polyurethanes, polyesters and polyamides.

In a further embodiment, it may be preferred to use at least one hydrophilic, film-forming polymer as sealing reagent (b1) in agent (b).

By a hydrophilic polymer is meant a polymer that has a solubility in water at 25° C. (760 mmHg) of more than 1% by weight, preferably more than 2% by weight.

The water solubility of the film-forming hydrophilic polymer can be determined, for example, in the following way. 1 g of the polymer is placed in a beaker. Water is added to make up to 100 g. A stirring bar is added and the mixture is heated to 25° C. on a magnetic stirrer with stirring. It is stirred for 60 minutes. The aqueous mixture is then visually assessed. A completely dissolved polymer appears macroscopically homogeneous. If the polymer-water mixture cannot be visually assessed due to high turbidity of the mixture, the mixture is filtered. If no undissolved polymer remains on the filter paper, then the solubility of the polymer is greater than 1% by weight.

Nonionic, anionic and cationic polymers can be used as film-forming, hydrophilic polymers.

Suitable film-forming hydrophilic polymers may be selected, for example, from the group comprising polyvinylpyrrolidone (co)polymers, polyvinyl alcohol (co)polymers, vinyl acetate (co)polymers, the carboxyvinyl (co)polymers, the acrylic acid (co)polymers, the methacrylic acid (co)polymers, the natural gums, the polysaccharides and/or the acrylamide (co)polymers.

Furthermore, it is particularly preferred to use polyvinylpyrrolidone (PVP) and/or a vinylpyrrolidone-containing copolymer as the film-forming hydrophilic polymer.

In another very particularly preferred embodiment, an agent (b) is exemplified in that it comprises at least one film-forming hydrophilic polymer selected from the group of polyvinylpyrrolidone (PVP) and the copolymers of polyvinylpyrrolidone.

It is further preferred if the agent contains polyvinylpyrrolidone (PVP) as the film-forming hydrophilic polymer. Surprisingly, the wash fastness of the stains obtained with PVP-containing agents (b) was also very good.

Particularly well-suited polyvinylpyrrolidones are available, for example, under the name Luviskol® K from BASF® SE, especially Luviskol® K 90 or Luviskol® K 85 from BASF® SE.

Another explicitly very suitable polyvinylpyrrolidone (PVP) can be the polymer PVP K30, which is sold by the company Ashland® (ISP, POI Chemical). PVP K 30 is a polyvinylpyrrolidone that is very soluble in cold water and has the CAS number 9003-39-8. The molecular weight of PVP K 30 is about 40000 g/mol.

Other particularly well-suited polyvinylpyrrolidones are the substances known under the trade names LUVITEC K 17, LUVITEC K 30, LUVITEC K 60, LUVITEC K 80, LUVITEC K 85, LUVITEC K 90 and LUVITEC K 115, which are available from BASF®.

The use of film-forming hydrophilic polymers (b1) from the group of copolymers of polyvinylpyrrolidone also led to particularly good and washfast color results.

In this context, vinylpyrrolidone-vinyl ester copolymers, such as those sold under the trademark Luviskol® (BASF®), can be mentioned as particularly suitable film-forming, hydrophilic polymers. Luviskol® VA 64 and Luviskol® VA 73, each vinylpyrrolidone/vinyl acetate copolymers, are particularly preferred nonionic polymers.

Of the vinylpyrrolidone-containing copolymers, a styrene/VP copolymer and/or a vinylpyrrolidone-vinyl acetate copolymer and/or a VP/DMAPA acrylates copolymer and/or a VP/vinyl caprolactam/DMAPA acrylates copolymer are very preferably used in the cosmetic compositions.

Vinylpyrrolidone-vinyl acetate copolymers are marketed by BASF® SE under the name Luviskol® VA. For example, a VP/vinyl caprolactam/DMAPA acrylates copolymer is sold under the trade name Aquaflex® SF-40 by Ashland® Inc. For example, a VP/DMAPA acrylates copolymer is marketed as Styleze® CC-10 by Ashland® and is a highly preferred vinylpyrrolidone-containing copolymer.

Other suitable copolymers of polyvinylpyrrolidone may include those obtained by reacting N-vinylpyrrolidone with at least one further monomer selected from the group of V-vinylformamide, vinyl acetate, ethylene, propylene, acrylamide, vinylcaprolactam, vinylcaprolactone and/or vinyl alcohol.

In another very particularly preferred embodiment, an agent (b) is exemplified in that it comprises at least one film-forming hydrophilic polymer (b1) selected from the group of polyvinylpyrrolidone (PVP), vinylpyrrolidone/vinyl acetate copolymers, Vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers.

Another suitable copolymer of vinylpyrrolidone is the polymer known under the INCI name maltodextrin/VP copolymer.

Furthermore, intensively colored keratinous material, especially hair, could be obtained with very good wash fastness properties when a nonionic film-forming hydrophilic polymer was used as the film-forming hydrophilic polymer.

In another embodiment, the agent (b) may comprise at least one nonionic film-forming hydrophilic polymer (b1).

As contemplated herein, a non-ionic polymer is a polymer which, in a protic solvent—such as water, for example—does not carry structural units with permanent cationic or anionic groups under standard conditions, which must be compensated by counterions while maintaining electroneutrality. Cationic groups include, for example, quaternized ammonium groups but not protonated amines. Anionic groups include, for example, carboxylic and sulfonic acid groups.

Agents are particularly preferred which contain, as nonionic, film-forming, hydrophilic polymer, at least one polymer selected from the group of Polyvinylpyrrolidone, Copolymers of N-vinylpyrrolidone and vinyl esters of carboxylic acids containing 2 to about 18 carbon atoms, in particular of N-vinylpyrrolidone and vinyl acetate, Copolymers of N-vinylpyrrolidone and N-vinylimidazole and methacrylamide, Copolymers of N-vinylpyrrolidone and N-vinylimidazole and acrylamide, Copolymers of N-vinylpyrrolidone with N,N-di(C1 to C4)alkylamino-(C2 to C4)alkyl acrylamide.

If copolymers of N-vinylpyrrolidone and vinyl acetate are used, it is again preferred if the molar ratio of the structural units contained from the monomer N-vinylpyrrolidone to the structural units of the polymer contained from the monomer vinyl acetate is in the range from about 20 to about 80 to about 80 to about 20, in particular from about 30 to about 70 to about 60 to about 40. Suitable copolymers of vinylpyrrolidone and vinyl acetate are available, for example, under the trademark Luviskol® VA 37, Luviskol® VA 55, Luviskol® VA 64 and Luviskol® VA 73 from BASF® SE.

Another particularly preferred polymer is selected from polymers with the INCI designation VP/Methacrylamide/Vinyl Imidazole Copolymer, which are available, for example, under the trade name Luviset® Clear from BASF® SE.

Another particularly preferred nonionic, film-forming, hydrophilic polymer is a copolymer of N-vinylpyrrolidone and N,N-dimethylaminiopropylmethacrylamide, which is sold, for example, by ISP under the INCI designation VP/DMAPA Acrylates Copolymer, e.g. under the trade name Styleze® CC 10.

A cationic polymer is the copolymer of N-vinylpyrrolidone, N-vinylcaprolactam, N-(3-dimethylaminopropyl) methacrylamide and 3-(methacryloylamino)propyl-lauryldimethylammonium chloride (INCI name: Polyquaternium-69), which is marketed, for example, under the trade name AquaStyle® 300 (28-32% by weight active substance in ethanol-water mixture, molecular weight 350000) by the company ISP.

Other suitable film-forming hydrophilic polymers include

Vinylpyrrolidone-vinylimidazolium methochloride copolymers as offered under the names Luviquat® FC 370, FC 550 and the INCI name Polyquaternium-16 as well as FC 905 and HM 552, Vinylpyrrolidone-vinylcaprolactam-acrylate terpolymers, such as those offered commercially with acrylic acid esters and acrylic acid amides as the third monomer building block, for example under the name Aquaflex® SF 40.

Polyquaternium-11 is the reaction product of diethyl sulfate with a copolymer of vinylpyrrolidone and dimethylaminoethyl methacrylate. Suitable commercial products are available, for example, under the names Dehyquart® CC 11 and Luviquat® PQ 11 PN from BASF® SE or Gafquat® 440, Gafquat® 734, Gafquat® 755 or Gafquat® 755N from Ashland® Inc.

Polyquaternium-46 is the reaction product of vinylcaprolactam and vinylpyrrolidone with methylvinylimidazolium methosulfate and is available, for example, under the name Luviquat® Hold from BASF® SE. Polyquaternium-46 is preferably used in an amount of 1 to 5% by weight—based on the total weight of the cosmetic composition. It is particularly preferred that polyquaternium-46 is used in combination with a cationic guar compound. In fact, it is highly preferred that polyquaternium-46 be used in combination with a cationic guar compound and polyquaternium-11.

Suitable anionic film-forming hydrophilic polymers can be, for example, acrylic acid polymers, which can be in uncrosslinked or crosslinked form. Corresponding products are sold commercially under the trade names Carbopol® 980, 981, 954, 2984 and 5984 by the company Lubrizol® or under the names Synthalen® M and Synthalen® K by the company 3V Sigma® (The Sun Chemicals, Inter Resin).

Examples of suitable film-forming, hydrophilic polymers from the group of natural gums are xanthan gum, gellan gum, carob gum.

Examples of suitable film-forming, hydrophilic polymers from the group of polysaccharides are hydroxyethyl cellulose, hydroxypropyl cellulose, ethyl cellulose and carboxymethyl cellulose.

Suitable film-forming, hydrophilic polymers from the group of acrylamides are, for example, polymers prepared from monomers of (meth)acrylamido-$C_1$-$C_4$-alkyl sulfonic acid or salts thereof. Corresponding polymers may be selected from the polymers of polyacrylamidomethanesulfonic acid, polyacrylamidoethanesulfonic acid, polyacrylamidopropanesulfonic acid, poly2-acrylamido-2-methylpropanesulfonic acid, poly-2-methylacrylamido-2-methylpropanesulfonic acid, and/or poly-2-methylacrylamido-n-butanesulfonic acid.

Preferred polymers of poly(meth)arylamido-$C_1$-$C_4$-alkyl-sulfonic acids are crosslinked and at least about 90% neutralized. These polymers can be crosslinked or uncrosslinked.

Cross-linked and fully or partially neutralized polymers of the poly-2-acrylamido-2-methylpropane sulfonic acid type are available under the INCI names "Ammonium Polyacrylamido-2-methyl-propanesulfonate" or "ammonium polyacryldimethyltauramide".

Another preferred polymer of this type is the crosslinked poly-2-acrylamido-2methyl-propanesulfonic acid polymer sold by Clariant® under the trade name Hostacerin® AMPS, which is partially neutralized with ammonia.

In another explicitly very particularly preferred embodiment, a process is exemplified in that the agent (b) comprises at least one anionic, film-forming, polymer (b1).

In this context, the best results were obtained when the agent (b) contains, as sealing reagent (b1), at least one film-forming polymer comprising at least one structural unit of formula (P-I) and at least one structural unit of formula (P-II)

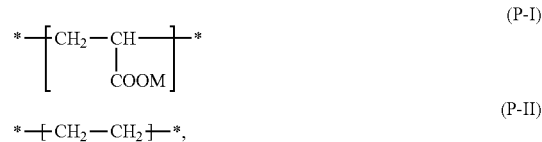

where
M represents a hydrogen atom or ammonium ($NH_4$), sodium, potassium, ½ magnesium or ½ calcium.

In a further preferred embodiment, a process is exemplified in that the agent (b) comprises at least one film-forming polymer as sealing reagent (b1), which comprises at least one structural unit of the formula (P-I) and at least one structural unit of the formula (P-II)

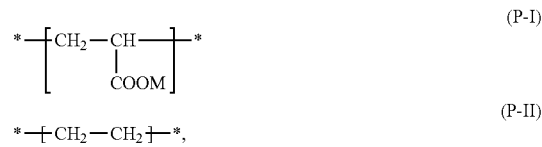

where
M represents a hydrogen atom or ammonium ($NH_4$), sodium, potassium, ½ magnesium or ½ calcium.

When M represents a hydrogen atom, the structural unit of the formula (P-I) is based on an acrylic acid unit.
When M stands for an ammonium counterion, the structural unit of the formula (P-I) is based on the ammonium salt of acrylic acid.
When M represents a sodium counterion, the structural unit of the formula (P-I) is based on the sodium salt of acrylic acid.
When M stands for a potassium counterion, the structural unit of the formula (P-I) is based on the potassium salt of acrylic acid.
If M stands for a half equivalent of a magnesium counterion, the structural unit of the formula (P-I) is based on the magnesium salt of acrylic acid.
If M stands for a half equivalent of a calcium counterion, the structural unit of the formula (P-I) is based on the calcium salt of acrylic acid.

The film-forming polymer or polymers (b1) are preferably used in certain ranges of amounts in the agent (b). In this context, it has proved particularly preferable to solve the problem as contemplated herein if the agent (b) contains—based on the total weight of the agent (b)—one or more film-forming polymers (b1) in a total amount of from about 0.1 to about 18% by weight, preferably from about 1 to about 16% by weight, more preferably from about 5 to about 14.5% by weight and very particularly preferably from about 8 to about 12% by weight.

In a further preferred embodiment, a process is exemplified in that the agent (b) contains—based on the total weight of the agent (b)—one or more film-forming polymers (b1) in a total amount of from about 0.1 to about 18% by weight, preferably from about 1 to about 16% by weight, more preferably from about 5 to about 14.5% by weight and very particularly preferably from about 8 to about 12% by weight.

The application of agent (b) comprising a film-forming polymer as sealing reagent (b1) is intended to seal and/or fix the colored film initially produced by the application of agent (a). With application of the second agent (b) with a film-forming polymer as sealing reagent (b1), the film-forming polymer (b1) is deposited on the colored film produced in the first layer in the form of a further film. The multilayer film system created in this way exhibits improved resistance to external influences.

Here, the film produced by the agent (b) comprising a film-forming polymer as sealing reagent (b1) is preferably not colored itself. In this way, it can also be ensured that any abrasion to a certain extent of the second film formed by agent (b) does not lead to any color changes in the entire film system. It is therefore particularly preferred if the agent (b) contains no or only very small amounts of colorant compounds.

In an alternative embodiment, the sealing reagent (b1) contains an alkalizing agent.

Particularly preferably, the alkalizing agent is selected from the group of ammonia, $C_2$-$C_6$ alkanolamines, basic amino acids, alkali metal hydroxides and alkaline earth metal hydroxides.

In another particularly preferred embodiment, a process is exemplified in that the agent (b) contains at least one alkalizing agent as sealing reagent (b1), which is selected from the group of ammonia, $C_2$-$C_6$ alkanolamines, basic amino acids, alkali metal hydroxides, alkaline earth metal hydroxides, alkali metal silicates, alkali metal metasilicates, alkaline earth metal silicates, alkaline earth metal metasilicates, alkali metal carbonates and alkaline earth metal carbonates.

It has been found that aftertreatment with an agent (b) containing ammonia exerts a particularly good influence on improving the wash fastness and rub fastness of the dyeings obtained in the process.

In the context of a further very particularly preferred embodiment, a method is exemplified in that the composition (b) comprises ammonia as sealing reagent (b1).

Good results were also obtained when composition (b) contained at least one $C_2$-$C_6$ alkanolamine as sealing reagent (b1).

The alkanolamines that can be used in composition (b) can be selected, for example, from the group of primary amines having a $C_2$-$C_6$ alkyl parent carrying at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol.

In a further preferred embodiment, a process as contemplated herein is exemplified in that the composition (b) comprises, as sealing reagent (b1), at least one alkalizing agent from the group of alkanolamines, which is preferably selected from the group of 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol and 2-amino-2-methylpropane-1,3-diol.

Likewise, good results were obtained when composition (b) contained at least one basic amino acid as sealing reagent (b1).

For the purposes of the present disclosure, an amino acid is an organic compound containing in its structure at least one protonatable amino group and at least one —COOH or one —SO$_3$H group. Preferred amino acids are aminocarboxylic acids, in particular α-(alpha)-aminocarboxylic acids and ω-aminocarboxylic acids, with α-aminocarboxylic acids being particularly preferred.

As contemplated herein, basic amino acids are those amino acids which have an isoelectric point pI of greater than about 7.0.

Basic α-aminocarboxylic acids contain at least one asymmetric carbon atom. In the context of the present disclosure, both possible enantiomers can be used equally as specific compounds or also mixtures thereof, in particular as racemates. However, it is particularly advantageous to use the naturally preferable isomeric form, usually in L-configuration.

The basic amino acids are preferably selected from the group formed by arginine, lysine, ornithine and histidine, particularly preferably arginine and lysine. In a further particularly preferred embodiment, the method is therefore exemplified in that the sealing reagent (b1) is an alkalizing agent comprising a basic amino acid selected from the group of arginine, lysine, ornithine and/or histidine.

In a further preferred embodiment, the method is exemplified in that the agent (b) comprises as sealing reagent (b1) at least one alkalizing agent selected from the group of basic amino acids, which is preferably selected from the group of arginine, lysine, ornithine and histidine.

Good results were also obtained when agent (b) contained at least one alkali metal hydroxide as sealing reagent (b1). Examples of well-suited alkali metal hydroxides are sodium hydroxide and potassium hydroxide.

Good results were also obtained when the composition (b) contained, as sealing reagent (b1), an alkalizing agent comprising at least one alkaline earth metal hydroxide. Suitable alkaline earth metal hydroxides include magnesium hydroxide, calcium hydroxide and barium hydroxide.

Good results were also obtained when the agent (b) contained at least one alkali metal silicate and/or alkali metal metasilicate as sealing reagent (b1). Suitable alkali metal silicates include sodium silicate and potassium silicate. Suitable alkali metal metasilicates include sodium metasilicate and potassium metasilicate.

Good results were also obtained when the agent (b) contained at least one alkali metal carbonate and/or alkaline earth metal carbonate as sealing reagent (b1). Suitable alkali metal carbonates include sodium carbonate and potassium carbonate. Suitable alkaline earth metal carbonates include magnesium carbonate and calcium carbonate.

Within the group of the aforementioned sealing reagents (b1) in the form of an alkalizing agent, ammonia, $C_2$-$C_6$ alkanolamines, basic amino acids and alkali metal hydroxides have proved to be particularly suitable.

In the context of a further particularly preferred embodiment, the process is exemplified in that the agent (b) comprises as sealing reagent (b1) at least one alkalizing agent selected from the group of ammonia, $C_2$-$C_6$ alkanolamines, basic amino acids and alkali metal hydroxides.

In another particularly preferred embodiment, the process is exemplified in that the agent (b) comprises as sealing reagent (b1) at least one alkalizing agent selected from the group of ammonia, 2-aminoethan-1-ol, 3-aminopropan-1-ol, 4-aminobutan-1-ol, 5-aminopentan-1-ol, 1-aminopropan-2- ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide and potassium hydroxide.

Composition (b) contains the alkalizing agent as a sealing reagent (b1) in a cosmetic carrier, preferably in an aqueous cosmetic carrier.

In this context, it has been found preferable if the agent (b) contains—based on the total weight of the agent (b)—about 5.0 to about 99.0% by weight, preferably about 15.0 to about 97.0% by weight, more preferably about 25.0 to about 97.0% by weight, still more preferably about 35.0 to about 97.0% by weight and very particularly preferably about 45.0 to about 97.0% by weight of water.

In the context of a further embodiment, the process is exemplified in that the agent (b) contains—based on the total weight of the agent (b)—about 5.0 to about 99.0% by weight, preferably about 15.0 to about 97.0% by weight, more preferably about 25.0 to about 97.0% by weight, still more preferably about 35.0 to about 97.0% by weight and very particularly preferably about 45.0 to about 97.0% by weight of water.

The alkalizing agents contained in the agent (b) exert an influence on the pH value of the agent (b). It was found that certain alkaline pH values in particular have a beneficial effect on the dyeing performance achievable in the process and the fastness properties of the dyeings.

For this reason, it is preferred that the agent (b) comprising an alkalizing agent as sealing reagent (b1) has a pH of from about 7.0 to about 12.0, preferably from about 7.5 to about 11.5, more preferably from about 8.0 to about 11.0, and most preferably from about 8.5 to about 9.5.

The pH value can be measured using the usual methods known from the state of the art, such as pH measurement using glass electrodes via combination electrodes or using pH indicator paper.

In another very particularly preferred embodiment, the process is exemplified in that the agent (b) contains an alkalizing agent as sealing reagent (b1) and has a pH of from about 7.0 to about 12.0, preferably from about 7.5 to about 11.5, more preferably from about 8.0 to about 11.0 and most preferably from about 8.5 to about 9.5.

The pH values for the purposes of the present disclosure are pH values measured at a temperature of 22° C.

In a still further alternative embodiment, the sealing reagent (b1) contains an acidifying agent.

Particularly preferably, the acidifying agent is selected from the group of inorganic acids, organic acids and mixtures thereof.

Good results could be obtained when agent (b) contains at least one inorganic acid as sealing reagent (b1). Suitable inorganic acids are, for example, phosphoric acid, sulfuric acid and/or hydrochloric acid, with sulfuric acid being particularly preferred.

In a further preferred embodiment, the process is exemplified in that the agent (b) comprises, as sealing reagent (b1), at least one acidifying agent selected from the group of inorganic acids, which is preferably selected from the group of phosphoric acid, sulfuric acid, hydrochloric acid and mixtures thereof.

In a further, even more preferred embodiment, the method is exemplified in that the agent (b) contains sulfuric acid as sealing reagent (b1).

Good results were also obtained when agent (b) contained at least one organic acid as sealing reagent (b1). The organic acid is preferably selected from the group of formic acid, acetic acid, propionic acid, butyric acid, isobutyric acid, valeric acid, isovaleric acid, pivalic acid, oxalic acid, malonic acid, succinic acid, glutaric acid, Glyceric acid, glyoxylic acid, adipic acid, pimelic acid, corkic acid, azelaic acid, sebacic acid, propiolic acid, crotonic acid, isocrotonic acid, elaidic acid, maleic acid, fumaric acid, muconic acid, citraconic acid, mesaconic acid, camphoric acid, benzoic acid, o,m,p-phthalic acid, naphthoic acid, toluoylic acid, hydratropic acid, atropic acid, cinnamic acid, isonicotinic acid, nicotinic acid, bicarbamic acid, 4,4'-dicyano-6,6'-binicotinic acid, 8-carbamoyloctanoic acid, 1,2,4-pentanetricarboxylic acid, 2-pyrrolecarboxylic acid, 1,2,4,6,7-napthalenepentaacetic acid, malonaldehyde acid, 4-hydroxy-phthalamic acid, 1-pyrazolecarboxylic acid, gallic acid or propane tricarboxylic acid, glycolic acid, gluconic acid, lactic acid, maleic acid, ascorbic acid, malic acid, tartaric acid, citric acid and mixtures thereof.

In a further preferred embodiment, the method is exemplified in that the agent (b) comprises as sealing reagent (b1) at least one acidifying agent selected from the group of organic acids, wherein the organic acid is preferably selected from the group of formic acid, Acetic acid, propionic acid, butyric acid, isobutyric acid, valeric acid, isovaleric acid, pivalic acid, oxalic acid, malonic acid, succinic acid, glutaric acid, glyceric acid, glyoxylic acid, adipic acid, pimelic acid, corkic acid, azelaic acid, sebacic acid, propiolic acid, crotonic acid, isocrotonic acid, elaidic acid, Maleic acid, fumaric acid, muconic acid, citraconic acid, mesaconic acid, camphoric acid, benzoic acid, o,m,p-phthalic acid, naphthoic acid, toluoylic acid, hydratropasic acid, atropasic acid, cinnamic acid, isonicotinic acid, nicotinic acid, bicarbamic acid, 4,4'-dicyano-6,6'-binicotinic acid, 8-carbamoyloctanoic acid, 1,2,4-pentane tricarboxylic acid, 2-pyrrole carboxylic acid, 1,2,4,6,7-napthalene pentaacetic acid, malonaldehyde acid, 4-hydroxy-phthalamic acid, 1-pyrazole carboxylic acid, gallic acid or propane tricarboxylic acid, glycolic acid, gluconic acid, lactic acid, maleic acid, ascorbic acid, malic acid, tartaric acid, citric acid and mixtures thereof.

In a further, even more preferred embodiment, the method is exemplified in that the agent (b) contains acetic acid as sealing reagent (b1).

Also suitable acidifiers include methanesulfonic acid and/or 1-hydroxyethane-1,1-diphosphonic acid.

Within the group of the above-mentioned sealing reagents (b1) in the form of an acidifying agent, sulfuric acid and/or acetic acid have proved to be particularly suitable.

In the context of a further particularly preferred embodiment, the process is exemplified in that the agent (b) comprises as sealing reagent (b1) at least one acidifying agent selected from the group of sulfuric acid, acetic acid and mixtures thereof.

Composition (b) contains the acidifying agent as sealing reagent (b1) in a cosmetic carrier, preferably in an aqueous cosmetic carrier.

The acidifying agents contained in the agent (b) exert an influence on the pH of the agent (b). It was found that acidic pH values also have a beneficial effect on the dyeing performance achievable in the process and the fastness properties of the dyeings.

For this reason, it is preferred that the agent (b) comprising an acidifying agent as sealing reagent (b1) has a pH of from about 2.0 to about 6.5, preferably from about 3.0 to about 6.0, more preferably from about 4.0 to about 6.0, and most preferably from about 4.5 to about 5.5.

The pH value can be measured using the usual methods known from the state of the art, such as pH measurement using glass electrodes via combination electrodes or using pH indicator paper.

In another very particularly preferred embodiment, the process is exemplified in that the agent (b) contains an acidifying agent as sealing reagent (b1) and has a pH of from about 2.0 to about 6.5, preferably from about 3.0 to about 6.0, more preferably from about 4.0 to about 6.0, and most preferably from about 4.5 to about 5.5.

The pH values for the purposes of the present disclosure are pH values measured at a temperature of 22° C.

Other ingredients in the agents (a) and (b)

The previously described agents (a) and (b) may further include one or more optional ingredients. However, it is essential to the present disclosure that at least one of the agents (a) and (b) further comprises at least one colorant compound selected from the group of pigments and/or direct dyes.

It may be preferred that, in addition to the at least one organic silicon compound selected from the group of silanes having one, two or three silicon atoms (a1), the at least one hydroxycarboxylic acid ester (a2) and the at least one diol (a3), the agent (a) further comprises at least one coloring compound selected from the group of pigments and/or direct dyes.

Alternatively, it may be preferred that the agent (b) further comprises, in addition to the sealing reagent (b1), at least one colorant compound selected from the group of pigments and/or direct dyes.

In an equally preferred embodiment of the process, the agent (a) and the agent (b) each further comprise at least one colorant compound selected from the group of pigments and/or direct dyes.

Irrespective of agents (a) and/or (b), the use of pigments has proved to be particularly preferred in this context.

In another very particularly preferred embodiment, a process is exemplified in that the agent (a) and/or the agent (b) further comprises at least one color-imparting compound selected from the group of pigments.

Pigments within the meaning of the present disclosure are colorant compounds which have a solubility in water at 25° C. of less than 0.5 g/L, preferably less than 0.1 g/L, still more preferably less than 0.05 g/L. Water solubility, for example, can be done using the method described below: 0.5 g of the pigment is weighed out in a beaker. A stirring bar is added. Then one liter of distilled water is added. This mixture is heated to 25° C. for one hour with stirring on a magnetic stirrer. If undissolved components of the pigment are still visible in the mixture after this period, the solubility of the pigment is below 0.5 g/L. If the pigment-water mixture cannot be visually assessed due to the high intensity of the pigment, which may be finely dispersed, the mixture is filtered. If a portion of undissolved pigment remains on the filter paper, the solubility of the pigment is below 0.5 g/L.

Suitable pigments can be of inorganic and/or organic origin.

In a preferred embodiment, a process is exemplified in that the agent (a) and/or the agent (b) further comprises at least one colorant compound selected from the group of inorganic and/or organic pigments.

Preferred pigments are selected from synthetic or natural inorganic pigments. Inorganic pigments of natural origin can be produced, for example, from chalk, ocher, umber, green earth, burnt terra di Siena or graphite. Furthermore, black pigments such as iron oxide black, colored pigments such as ultramarine or iron oxide red, and fluorescent or phosphorescent pigments can be used as inorganic pigments.

Particularly suitable are colored metal oxides, hydroxides and oxide hydrates, mixed-phase pigments, sulfur-containing silicates, silicates, metal sulfides, complex metal cyanides, metal sulfates, chromates and/or molybdates. Particularly preferred pigments are black iron oxide (CI 77499), yellow iron oxide (CI 77492), red and brown iron oxide (CI 77491), manganese violet (CI 77742), ultramarines (sodium aluminum sulfosilicates, CI 77007, Pigment Blue 29), chromium oxide hydrate (CI77289), iron blue (ferric ferrocyanide, CI77510) and/or carmine (cochineal).

Also particularly preferred pigments are colored pearlescent pigments. These are usually mica and/or mica-based and may be coated with one or more metal oxides. Mica belongs to the layer silicates. The main representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

Accordingly, a preferred process is exemplified in that the agent (a) and/or the agent (b) further comprises at least one colorant compound selected from the group of pigments selected from the group of colored metal oxides, metal hydroxides, metal oxide hydrates, silicates, metal sulfides, complex metal cyanides, metal sulfates, bronze pigments and/or colored pigments based on natural or synthetic mica coated with at least one metal oxide and/or a metal oxychloride.

In a further preferred embodiment, the process is characterized in that the agent (a) and/or the agent (b) comprises at least one colorant compound from the group of pigments selected from pigments based on natural or synthetic mica which are reacted with one or more metal oxides from the group comprising titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

A preferred suitable pigment based on synthetic mica is, for example, Timiron® SynWhite Satin from Merck®.

Other suitable pigments are based on metal oxide-coated platelet-shaped borosilicates. These are coated, for example, with tin oxide, iron oxide(s), silicon dioxide and/or titanium dioxide coated. Such borosilicate-based pigments are available, for example, under the name MIRAGE from Eckart® or Reflecks from BASF® SE.

In a preferred embodiment, agent (a) is exemplified in that it comprises at least one coloring compound selected from the group of inorganic pigments, black iron oxide (CI 77499), yellow iron oxide (CI 77492), red iron oxide (CI 77491) and mixtures thereof.

Yellow iron oxide (or iron oxide yellow) is the name for FeO(OH), in the color index under C.I. Pigment Yellow 42 listed.

Red iron oxide (or iron oxide red) is the name for $Fe_2O_3$, in the color index under C.I. Pigment Red 101 listed. Depending on the particle size, red iron oxide pigments can be adjusted to be very yellowish (small particle size) to very blueish (coarse particles).

Black iron oxide (or iron oxide black) is listed in the Color Index under C.I. Pigment Black 11. Iron oxide black is ferromagnetic. The chemical formula is often given as $Fe_3O_4$, in reality there is a solid solution of $Fe_2O_3$ and FeO with inverse spinel structure. Further black pigments are obtained by doping with chromium, copper or manganese.

Brown Black Iron Oxide (or Iron Oxide Brown) usually does not refer to a defined pigment, but to a mixture of yellow, red and/or black iron oxide.

Iron oxide pigments usually have particle diameters in the range of 2,000 to 4,000 nm. For some applications, especially for cosmetic purposes, it may be advantageous to use iron oxide pigments with significantly smaller particle diameters. For example, hair dyes with iron oxide pigments that have a particle diameter in the range of about 100 to about 1,000 nm, more preferably about 150 nm about 700 nm, show better durability and better gray coverage.

Even more preferred, therefore, is an agent (a), which further comprises a colorant compound selected from the group of pigments and/or direct dyes, wherein the colorant compound comprises a pigment selected from the group of iron oxide pigments, and wherein the iron oxide pigment has a particle diameter in the range from about 100 to about 1,000 nm, more preferably about 150 nm about 700 nm.

Examples of particularly suitable pigments are commercially available under the trade names Rona®, Colorona®, Xirona®, Dichrona® and Timiron® from Merck®, Ariabel® and Unipure® from Sensient®, Prestige® or SynCrystal® from Eckart® Cosmetic Colors, Flamenco®, Cellini®, Cloisonné®, Duocrome®, Gemtone®, Timica®, MultiReflections, Chione from BASF® SE and Sunshine® from Sunstar®.

Very particularly preferred pigments with the trade name Colorona® are, for example:
- Colorona® Copper, Merck®, MICA, CI 77491 (IRON OXIDES)
- Colorona® Copper Fine, Merck®, MICA, CI 77491 (IRON OXIDES)
- Colorona® Passion Orange, Merck®, Mica, CI 77491 (Iron Oxides), Alumina
- Colorona® Patina Silver, Merck®, MICA, CI 77499 (IRON OXIDES), CI 77891 (TITANIUM DIOXIDE)
- Colorona® RY, Merck®, CI 77891 (TITANIUM DIOXIDE), MICA, CI 75470 (CARMINE)
- Colorona® Oriental Beige, Merck®, MICA, CI 77891 (TITANIUM DIOXIDE), CI 77491 (IRON OXIDES)
- Colorona® Dark Blue, Merck®, MICA, TITANIUM DIOXIDE, FERRIC FERROCYANIDE
- Colorona® Chameleon, Merck®, CI 77491 (IRON OXIDES), MICA
- Colorona® Aboriginal Amber, Merck®, MICA, CI 77499 (IRON OXIDES), CI 77891 (TITANIUM DIOXIDE)
- Colorona® Blackstar Blue, Merck®, CI 77499 (IRON OXIDES), MICA
- Colorona® Patagonian Purple, Merck®, MICA, CI 77491 (IRON OXIDES), CI 77891 (TITANIUM DIOXIDE), CI 77510 (FERRIC FERROCYANIDE)
- Colorona® Red Brown, Merck®, MICA, CI 77491 (IRON OXIDES), CI 77891 (TITANIUM DIOXIDE)
- Colorona® Russet, Merck®, CI 77491 (TITANIUM DIOXIDE), MICA, CI 77891 (IRON OXIDES)
- Colorona® Imperial Red, Merck®, MICA, TITANIUM DIOXIDE (CI 77891), D&C RED NO. 30 (CI 73360)
- Colorona® Majestic Green, Merck®, CI 77891 (TITANIUM DIOXIDE), MICA, CI 77288 (CHROMIUM OXIDE GREENS)
- Colorona® Light Blue, Merck®, MICA, TITANIUM DIOXIDE (CI 77891), FERRIC FERROCYANIDE (CI 77510)
- Colorona® Red Gold, Merck®, MICA, CI 77891 (TITANIUM DIOXIDE), CI 77491 (IRON OXIDES)
- Colorona® Gold Plus MP 25, Merck®, MICA, TITANIUM DIOXIDE (CI 77891), IRON OXIDES (CI 77491)
- Colorona® Carmine Red, Merck®, MICA, TITANIUM DIOXIDE, CARMINE
- Colorona® Blackstar Green, Merck®, MICA, CI 77499 (IRON OXIDES)
- Colorona® Bordeaux, Merck®, MICA, CI 77491 (IRON OXIDES)
- Colorona® Bronze, Merck®, MICA, CI 77491 (IRON OXIDES)
- Colorona® Bronze Fine, Merck®, MICA, CI 77491 (IRON OXIDES)
- Colorona® Fine Gold MP 20, Merck®, MICA, CI 77891 (TITANIUM DIOXIDE), CI 77491 (IRON OXIDES)
- Colorona® Sienna Fine, Merck®, CI 77491 (IRON OXIDES), MICA
- Colorona® Sienna, Merck®, MICA, CI 77491 (IRON OXIDES)
- Colorona® Precious Gold, Merck®, Mica, CI 77891 (Titanium dioxide), Silica, CI 77491 (Iron oxides), Tin oxide
- Colorona® Sun Gold Sparkle MP 29, Merck®, MICA, TITANIUM DIOXIDE, IRON OXIDES, MICA, CI 77891, CI 77491 (EU)
- Colorona® Mica Black, Merck®, CI 77499 (Iron oxides), Mica, CI 77891 (Titanium dioxide)
- Colorona® Bright Gold, Merck®, Mica, CI 77891 (Titanium dioxide), CI 77491 (Iron oxides)
- Colorona® Blackstar Gold, Merck®, MICA, CI 77499 (IRON OXIDES)
- Colorona® SynCopper, Merck®, Synthetic Fluorphlogopite (and) Iron Oxides
- Colorona® SynBronze, Merck®, Synthetic Fluorphlogopite (and) Iron Oxides.

Further particularly preferred pigments with the trade name Xirona® are, for example:
- Xirona® Golden Sky, Merck®, Silica, CI 77891 (Titanium Dioxide), Tin Oxide
- Xirona® Caribbean Blue, Merck®, Mica, CI 77891 (Titanium Dioxide), Silica, Tin Oxide
- Xirona® Kiwi Rose, Merck®, Silica, CI 77891 (Titanium Dioxide), Tin Oxide
- Xirona® Magic Mauve, Merck®, Silica, CI 77891 (Titanium Dioxide), Tin Oxide
- Xirona® Le Rouge, Merck®, iron Oxides. (and) Silica.

In addition, particularly preferred pigments with the trade name Unipure® are, for example:
- Unipure® Red LC 381 EM, Sensient® CI 77491 (Iron Oxides), Silica
- Unipure® Black LC 989 EM, Sensient®, CI 77499 (Iron Oxides), Silica
- Unipure® Yellow LC 182 EM, Sensient®, CI 77492 (Iron Oxides), Silica.

Also particularly preferred pigments with the trade name Flamenco® are, for example:
- Flamenco® Summit Turquoise T30D, BASF®, Titanium Dioxide (and) Mica
- Flamenco® Super Violet 530Z, BASF®, Mica (and) Titanium Dioxide.

In a further embodiment, the agent (a) and/or agent (b) used in the process may also comprise one or more colorant compounds from the group of organic pigments.

The organic pigments are correspondingly insoluble organic dyes or colorants which may be selected, for example, from the group of nitroso, nitro-azo, xanthene, anthraquinone, isoindolinone, isoindoline, quinacridone, perinone, perylene, diketopyrrolopyrrole, indigo, thioindigo, dioxazine and/or triarylmethane compounds.

Particularly suitable organic pigments are, for example, carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, the process is exemplified in that the agent (a) and/or the agent (b) comprises at least one colorant compound from the group of organic pigments selected from the group of carmine, quinacridone, phthalocyanine, sorghum, blue pigments having the Color Index numbers CI 42090, CI 69800, CI 69825, CI 73000, CI 74100, CI 74160, yellow pigments having the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof.

The organic pigment can also be a colored paint. As contemplated herein, the term color varnish means particles comprising a layer of absorbed dyes, the unit of particle and dye being insoluble under the above conditions. The particles may be, for example, inorganic substrates, which may be aluminum, silica, calcium borosilicate, calcium aluminum borosilicate, or aluminum.

Alizarin color varnish, for example, can be used as a color varnish.

In a further embodiment of the process, the agent (a) and/or the agent (b) may also contain one or more colorant compounds from the group of organic pigments.

In another particularly preferred embodiment, a process is exemplified in that the agent (a) and/or the agent (b) comprises at least one colorant compound from the group of organic pigments selected from the group of carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

Also suitable colorant compounds from the group of pigments are inorganic and/or organic pigments modified with a polymer. The polymer modification can, for example, increase the affinity of the pigments to the respective material of the at least one layer.

In the agent (a) and/or the agent (b), so-called metal effect pigments can also be used as color-imparting compound.

In particular, the metal effect pigments may include pigments based on a lamellar substrate platelet, pigments based on lenticular substrate platelets, and/or pigments based on substrate platelets comprising "vacuum metallized pigments" (VMP). In these metal effect pigments, the substrate platelets comprise a metal, preferably aluminum, or an alloy. Metal substrate platelet-based metal effect pigments preferably have a coating which, among other things, acts as a protective layer.

Suitable metallic effect pigments include, for example, the pigments Alegrace® Marvelous, Alegrace® Gorgeous or Alegrace® Aurous from Schlenk® Metallic Pigments.

Also suitable metal effect pigments are the aluminum-based pigments of the SILVERDREAM® series and the pigments based on aluminum or on copper/zinc-containing metal alloys of the VISIONAIRE® series from Eckart®.

Due to their excellent light and temperature stability, the use of the above pigments in agent (a) and/or (b) is particularly preferred. Furthermore, it is preferred if the pigments used have a certain particle size. On the one hand, this particle size leads to an even distribution of the pigments in the polymer film formed and, on the other hand, avoids a rough hair or skin feeling after application of the cosmetic product. It is therefore advantageous as contemplated herein if at least one pigment has an average particle size D50 of from about 1 to about 50 μm, preferably from about 5 to about 45 μm, preferably from about 10 to about 40 μm, in particular from about 14 to about 30 μm. For example, the average particle size D50 can be determined using dynamic light scattering (DLS).

In a further preferred embodiment, the process is exemplified in that the agent (a)—based on the total weight of the agent (a)—further comprises one or more color-imparting compound(s) in the form of pigments in a total amount of from about 0.01 to about 10% by weight, preferably from about 0.1 to about 8% by weight, more preferably from about 0.2 to about 6% by weight and most preferably from about 0.5 to about 4.5% by weight.

In a further, likewise preferred embodiment, the process is exemplified in that the agent (b)—based on the total weight of the agent (b)—further comprises one or more color-imparting compound(s) in the form of pigments in a total amount of from about 0.01 to about 10% by weight, preferably from about 0.1 to about 8% by weight, more preferably from about 0.2 to about 6% by weight and very particularly preferably from about 0.5 to about 4.5% by weight.

As colorant compound(s), the agents (a) and/or agents (b) used in the process may also contain one or more direct dyes. Direct-acting dyes are dyes that draw directly onto the hair and do not require an oxidative process to form the color. Direct dyes are usually nitrophenylenediamines, nitroaminophenols, azo dyes, anthraquinones, triarylmethane dyes or indophenols.

The direct dyes according to the present disclosure have a solubility in water (760 mmHg) at 25° C. of more than 0.5 g/L and are therefore not to be regarded as pigments.

Preferably, the direct dyes according to the present disclosure have a solubility in water (760 mmHg) at 25° C. of greater than 1 g/L.

Direct dyes can be divided into anionic, cationic and nonionic direct dyes.

In a further preferred embodiment, the process is exemplified in that the agent (a) and/or the agent (b) further comprises as coloring compound at least one anionic, cationic and/or nonionic direct dye.

In a further preferred embodiment, the process is exemplified in that the agent (a) and/or the agent (b) further comprises at least one colorant compound selected from the group of anionic, nonionic, and/or cationic direct dyes.

Suitable cationic direct dyes include Basic Blue 7, Basic Blue 26, Basic Violet 2 and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51, and Basic Red 76.

Examples of nonionic direct dyes that can be used are nonionic nitro and quinone dyes and neutral azo dyes. Suitable nonionic direct dyes are those available under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-1(4-amino-2-nitrophenyl)aminol-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid, and 2-chloro-6-ethylamino-4-nitrophenol.

In the course of the work leading to the present disclosure, it has been found that dyeings of particularly high color intensity can be produced in particular with agents (a) and/or (b) containing at least one anionic direct dye.

In an explicitly quite particularly preferred embodiment, the process is therefore exemplified in that the agent (a) and/or the agent (b) further comprises at least one anionic direct dye as colorant compound.

Anionic direct dyes are also called acid dyes. Acid dyes are direct dyes that have at least one carboxylic acid moiety (—COOH) and/or one sulfonic acid moiety (—$SO_3H$). Depending on the pH, the protonated forms (—COOH, —$SO_3H$) of the carboxylic or sulfonic acid moieties are in equilibrium with their deprotonated forms (—COO—, —$SO_3$— present). As pH decreases, the proportion of protonated forms increases. If direct dyes are used in the form of their salts, the carboxylic acid groups or sulfonic acid groups are present in deprotonated form and are neutralized with corresponding stoichiometric equivalents of cations to maintain electroneutrality. The acid dyes can also be used in the form of their sodium salts and/or their potassium salts.

The acid dyes according to the present disclosure have a solubility in water (760 mmHg) at 25° C. of more than 0.5 g/L and are therefore not to be considered pigments. Preferably, the acid dyes according to the present disclosure have a solubility in water (760 mmHg) at 25° C. of greater than 1 g/L.

The alkaline earth salts (such as calcium salts and magnesium salts) or aluminum salts of acid dyes often have poorer solubility than the corresponding alkali salts. If the solubility of these salts is below 0.5 g/L (25° C., 760 mmHg), they do not fall under the definition of a direct dye.

A key feature of acid dyes is their ability to form anionic charges, with the carboxylic or sulfonic acid groups responsible for this usually being attached to various chromophoric systems. Suitable chromophoric systems are found, for example, in the structures of nitrophenylenediamines, nitroaminophenols, azo dyes, anthraquinone dyes, triarylmethane dyes, xanthene dyes, rhodamine dyes, oxazine dyes, and/or indophenol dyes.

In the context of one embodiment, a process for dyeing keratinous material is thus preferred, which is exemplified in that the agent (a) and/or the agent (b) further comprises at least one anionic direct dye as coloring compound, which is selected from the group of the nitrophenylenediamines, the nitroaminophenols, the azo dyes, the anthraquinone dyes, the triarylmethane dyes, the xanthene dyes, the rhodamine dyes, the oxazine dyes and/or the indophenol dyes, the dyes from the above-mentioned group each containing at least one carboxylic acid group (—COOH), a sodium carboxylate group (—COONa), a potassium carboxylate group (—COOK), a sulfonic acid group (—$SO_3H$), a sodium sulfonate group (—$SO_3Na$) and/or a potassium sulfonate group (—$SO_3K$).

For example, one or more compounds from the following group can be selected as particularly well-suited acid dyes: Acid Yellow 1 (D&C Yellow 7, Citronin A, Ext. D&C Yellow No. 7, Japan Yellow 403, CI 10316, COLIPA no B001), Acid Yellow 3 (COLIPA no: C 54, D&C Yellow No 10, Quinoline Yellow, E104, Food Yellow 13), Acid Yellow 9 (CI 13015), Acid Yellow 17 (CI 18965), Acid Yellow 23 (COLIPA no C. 29, Covacap Jaune W 1100 (LCW), Sicovit Tartrazine 85 E 102 (BASF®), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-naphthol orange, Orange II, CI 15510, D&C Orange 4, COLIPA no C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C Red 46, True Red D, FD&C Red No. 2, Food Red 9, Naphthol Red S), Acid Red 33 (Red 33, Fuchsia Red, D&C Red 33, CI 17200), Acid Red 35 (CI C.I. 18065), Acid Red 51 (CI 45430, Pyrosine B, Tetraiodofluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI 27290), Acid Red 87 (Eosin, CI 45380), Acid Red 92 (COLIPA no C53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet no 2, C.I. 60730, COLIPA no C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido Blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (C.I. 42100), Acid Green 22 (C.I. 42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black n° 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The water solubility of anionic direct dyes can be determined, for example, in the following way. 0.1 g of the anionic direct dye is added to a beaker. A stirring bar is added. Then 100 ml of water is added. This mixture is heated to 25° C. on a magnetic stirrer while stirring. It is stirred for 60 minutes. The aqueous mixture is then visually assessed. If undissolved residues are still present, the amount of water is increased—for example in steps of 10 ml. Water is added until the amount of dye used has completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml of water at 25° C., the solubility of the dye is 1 g/L.

Acid Yellow 1 is named 8-hydroxy-5,7-dinitro-2-naphthalenesulfonic acid disodium salt and has a solubility in water of at least 40 g/L (25° C.).

Acid Yellow 3 is a mixture of the sodium salts of mono- and disulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, and its water solubility is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and is readily soluble in water at 25° C.

Acid Orange 7 is the sodium salt of 4-[(2-hydroxy-1-naphthyl)azo]benzenesulfonate. Its solubility in water is more than 7 g/L (25° C.).

Acid Red 18 is the trisodium salt of 7-hydroxy-8-[(E)-(4-sulfonato-1-naphthyl)-diazenyl]-1,3-naphthalene-disulfonate and has a very high water solubility of more than 20% by weight.

Acid Red 33 is the disodium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is reported to be greater than 10 g/L (25° C.).

Acid Blue 9 is the disodium salt of 2-({4-[N-ethyl(3-sulfonatobenzyl)amino]phenyl}{4-[(N-ethyl(3-sulfonatobenzyl)imino]-2,5-cyclohexadien-1-ylidene}methyl)-benzenesulfonate and has a water solubility greater than 20% by weight (25° C.).

A very particularly preferred process is therefore exemplified in that the agent (a) and/or the agent (b) further contains at least one colorant compound from the group of anionic direct dyes selected from the group of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

The direct dye(s), in particular the anionic direct dyes, can be used in different amounts in the agent (a) and/or the agent (b) depending on the desired color intensity. Particularly good results were obtained when the agent (a) and/or the agent (b)—in each case based on its total weight—also contains one or more direct dyes as colorant compound in a total amount of from about 0.01 to about 10% by weight, preferably from about 0.1 to about 8% by weight, more preferably from about 0.2 to about 6% by weight and very particularly preferably from about 0.5 to about 4.5% by weight.

In a further preferred embodiment, the process is exemplified in that the agent (a) and/or the agent—based on the total weight of the agent (a) and/or the agent (b)—further comprises one or more direct dyes as colorant compound in a total amount of from about 0.01 to about 10% by weight, preferably from about 0.1 to about 8% by weight, more preferably from about 0.2 to about 6% by weight and most preferably from about 0.5 to about 4.5% by weight.

The following discloses preferred embodiments of the method with respect to the color-imparting compounds:

1. A method for dyeing keratinous material, in particular human hair, comprising the following steps:
    Application of an agent (a) to the keratinous material, wherein the agent (a) comprises:
    (a1) at least one organic silicon compound selected from the group of silanes having one, two or three silicon atoms,
    (a2) at least one hydroxycarboxylic acid ester,
    (a3) at least one diol and
    (a4) at least one coloring compound comprising at least one inorganic pigment selected from the group of colored metal oxides, metal hydroxides, metal oxide hydrates, silicates, metal sulfides, complex metal cyanides, metal sulfates, bronze pigments and mixtures thereof,
    Application of an agent (b) to the keratinous material, wherein the agent (b) comprises:
    (b1) at least one sealing reagent.

2. A method for dyeing keratinous material, in particular human hair, comprising the following steps:
    Application of an agent (a) to the keratinous material, wherein the agent (a) comprises:
    (a1) at least one organic silicon compound selected from the group of silanes having one, two or three silicon atoms,
    (a2) at least one hydroxycarboxylic acid ester,
    (a3) at least one diol and
    (a4) at least one coloring compound comprising at least one inorganic pigment selected from the group of colored metal oxides, metal hydroxides, metal oxide hydrates, silicates, metal sulfides, complex metal cyanides, metal sulfates, Bronze pigments and mixtures thereof and at least one pigment selected from the group of pigments based on a lamellar metallic substrate platelet, pigments based on a lenticular metallic substrate platelet, pigments based on a metallic substrate platelet comprising a vacuum metallized pigment (VMP) and mixtures thereof,
    Application of an agent (b) to the keratinous material, wherein the agent (b) comprises:
    (b1) at least one sealing reagent.

3. A method for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one hydroxycarboxylic acid ester,
(a3) at least one diol and
(a4) at least one colorant compound comprising at least one inorganic pigment selected from the group of colored metal oxides, metal hydroxides, metal oxide hydrates, silicates, metal sulfides, complex metal cyanides, metal sulfates, bronze pigments, and mixtures thereof, and at least one pigment comprising a) a substrate platelet comprising mica, and β) a coating comprising at least one first metal oxide (hydrate) layer comprising $TiO_2$, $SnO_2$ and/or iron oxide(s),
Application of an agent (b) to the keratinous material, wherein the agent (b) comprises:
(b1) at least one sealing reagent.

4. A method for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one hydroxycarboxylic acid ester,
(a3) at least one diol and
(a4) at least one coloring compound comprising at least one inorganic pigment selected from the group of colored metal oxides, metal hydroxides, metal oxide hydrates, silicates, metal sulfides, complex metal cyanides, metal sulfates, bronze pigments and mixtures thereof,
Application of an agent (b) to the keratinous material, wherein the agent (b) comprises:
(b1) at least one sealing reagent comprising a film-forming polymer, and
(b2) at least one colorant compound comprising at least one pigment selected from the group of lamellar metallic substrate platelet-based pigments, lenticular metallic substrate platelet-based pigments, metallic substrate platelet-based pigments comprising a vacuum metallized pigment (VMP), and mixtures thereof.

5. A method for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one hydroxycarboxylic acid ester,
(a3) at least one diol and
(a4) at least one coloring compound comprising at least one inorganic pigment selected from the group of colored metal oxides, metal hydroxides, metal oxide hydrates, silicates, metal sulfides, complex metal cyanides, metal sulfates, bronze pigments and mixtures thereof,
Application of an agent (b) to the keratinous material, wherein the agent (b) comprises:
(b1) at least one sealing reagent comprising a film-forming polymer, and
(b2) at least one colorant compound comprising a pigment comprising α) a substrate platelet comprising mica, and β) a coating comprising at least a first metal oxide (hydrate) layer comprising $TiO_2$, $SnO_2$ and/or iron oxide(s).

6. A method for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one hydroxycarboxylic acid ester,
(a3) at least one diol and
(a4) at least one coloring compound comprising at least one inorganic pigment selected from the group of colored metal oxides, metal hydroxides, metal oxide hydrates, silicates, metal sulfides, complex metal cyanides, metal sulfates, bronze pigments and mixtures thereof,
Application of an agent (b) to the keratinous material, wherein the agent (b) comprises:
(b1) at least one sealing reagent comprising a film-forming polymer, and
(b2) at least one colorant compound comprising a pigment comprising α) a substrate platelet comprising borosilicate glass, and β) a coating comprising at least a first metal oxide (hydrate) layer comprising $TiO_2$, $SnO_2$, $SiO_2$, and/or iron oxide(s).

7. A method for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one hydroxycarboxylic acid ester,
(a3) at least one diol and
(a4) at least one coloring compound comprising at least one organic pigment selected from the group of carmine, quinacridone, phthalocyanine, sorghum, blue pigments having the color index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof,
Application of an agent (b) to the keratinous material, wherein the agent (b) comprises:
(b1) at least one sealing reagent.

8. A method for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one hydroxycarboxylic acid ester, (a3) at least one diol and
(a4) at least one colorant compound comprising at least one organic pigment selected from the group of carmine, quinacridone, phthalocyanine, sorghum, blue pigments having the color index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof, and at least one pigment selected from the group of pigments based on a lamellar metallic substrate platelet, pigments based on a lenticular metallic substrate platelet, pigments based on a metallic substrate platelet comprising a vacuum metallized pigment (VMP), and mixtures thereof,
Application of an agent (b) to the keratinous material, wherein the agent (b) comprises:
(b1) at least one sealing reagent.

9. A method for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one hydroxycarboxylic acid ester,
(a3) at least one diol and
(a4) at least one colorant compound comprising at least one organic pigment selected from the group of carmine, quinacridone, phthalocyanine, sorghum, blue pigments having the color index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof, and at least one pigment comprising α) a substrate platelet comprising mica, and β) a coating comprising at least a first metal oxide (hydrate) layer comprising TiO2, SnO2 and/or iron oxide(s),
Application of an agent (b) to the keratinous material, wherein the agent (b) comprises:
(b1) at least one sealing reagent.

10. A method for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one hydroxycarboxylic acid ester,
(a3) at least one diol and
(a4) at least one coloring compound comprising at least one organic pigment selected from the group of carmine, quinacridone, phthalocyanine, sorghum, blue pigments having the color index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof,
Application of an agent (b) to the keratinous material, wherein the agent (b) comprises:
(b1) at least one sealant reagent comprising a film-forming polymer, and
(b2) at least one colorant compound comprising at least one pigment selected from the group of lamellar metallic substrate platelet-based pigments, lenticular metallic substrate platelet-based pigments, metallic substrate platelet-based pigments comprising a vacuum metallized pigment (VMP), and mixtures thereof.

11. A method for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one hydroxycarboxylic acid ester,
(a3) at least one diol and
(a4) at least one coloring compound comprising at least one organic pigment selected from the group of carmine, quinacridone, phthalocyanine, sorghum, blue pigments having the color index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof,
Application of an agent (b) to the keratinous material, wherein the agent (b) comprises:
(b1) at least one sealing reagent comprising a film-forming polymer, and
(b2) at least one colorant compound comprising a pigment comprising α) a substrate platelet comprising mica, and β) a coating comprising at least a first metal oxide (hydrate) layer comprising $TiO_2$, $SnO_2$ and/or iron oxide(s).

12. A method for dyeing keratinous material, in particular human hair, comprising the following steps:
Application of an agent (a) to the keratinous material, wherein the agent (a) comprises:

(a1) at least one organic silicon compound selected from the group of silanes having one, two or three silicon atoms,
(a2) at least one hydroxycarboxylic acid ester,
(a3) at least one diol and
(a4) at least one coloring compound comprising at least one organic pigment selected from the group of carmine, quinacridone, phthalocyanine, sorghum, blue pigments having the color index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470 and mixtures thereof,
Application of an agent (b) to the keratinous material, wherein the agent (b) comprises:
(b1) at least one sealing reagent comprising a film-forming polymer, and
(b2) at least one colorant compound comprising a pigment comprising α) a substrate platelet comprising borosilicate glass, and β) a coating comprising at least a first metal oxide (hydrate) layer comprising $TiO_2$, $SnO_2$, $SiO_2$, and/or iron oxide(s).

13. A method for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one hydroxycarboxylic acid ester and
(a3) at least one diol
Application of an agent (b) to the keratinous material, wherein the agent (b) comprises:
(b1) at least one sealing reagent comprising a film-forming polymer, and
(b2) at least one colorant compound comprising at least one pigment selected from the group of lamellar metallic substrate platelet-based pigments, lenticular metallic substrate platelet-based pigments, metallic substrate platelet-based pigments comprising a vacuum metallized pigment (VMP), and mixtures thereof.

14. A method for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one hydroxycarboxylic acid ester,
(a3) at least one diol and
(a4) at least one colorant compound selected from the group of pigments and/or direct dyes, comprising a pigment selected from the group of iron oxide pigments, the iron oxide pigment having a particle diameter in the range from about 100 to about 1,000 nm, more preferably about 150 nm about 700 nm,
Application of an agent (b) to the keratinous material, wherein the agent (b) comprises:
(b1) at least one sealing reagent.

15. A method for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one hydroxycarboxylic acid ester, and
(a3) at least one diol and
(a4) at least one colorant compound selected from the group of pigments and/or direct dyes, comprising a pigment selected from the group of iron oxide pigments, the iron oxide pigment having a particle diameter in the range from about 100 to about 1,000 nm, more preferably about 150 nm about 700 nm, and at least one pigment selected from the group of pigments based on a lamellar metallic substrate platelet, pigments based on a lenticular metallic substrate platelet, pigments based on a metallic substrate platelet comprising a "vacuum metallized pigment" (VMP), and mixtures thereof,
Application of an agent (b) to the keratinous material, wherein the agent (b) comprises:
(b1) at least one sealing reagent.

16. A method for dyeing keratinous material, in particular human hair, comprising the following steps:
Application of an agent (a) to the keratinous material, wherein the agent (a) comprises:
(a1) at least one organic silicon compound selected from the group of silanes having one, two or three silicon atoms,
(a2) at least one hydroxycarboxylic acid ester, and
(a3) at least one diol and
(a4) comprises at least one colorant compound selected from the group of pigments and/or direct dyes, comprising a pigment selected from the group of iron oxide pigments, and where the iron oxide pigment has a particle diameter in the range from about 100 to about 1,000 nm, more preferably about 150 nm about 700 nm,
Application of an agent (b) to the keratinous material, wherein the agent (b) comprises:
(b1) at least one sealing reagent comprising a film-forming polymer, and
(b2) at least one colorant compound selected from the group of pigments and/or direct dyes, comprising at least one pigment selected from the group of pigments based on a lamellar metallic substrate platelet, pigments based on a lenticular metallic substrate platelet, pigments based on a metallic substrate platelet comprising a vacuum metallized pigment (VMP), and mixtures thereof.

The agents may additionally contain one or more surfactants. The term surfactants is used to describe surface-active substances. A distinction is made between anionic surfactants comprising a hydrophobic radical and a negatively charged hydrophilic head group, amphoteric surfactants, which carry both a negative and a compensating positive charge, cationic surfactants, which have a positively charged hydrophilic group in addition to a hydrophobic radical, and nonionic surfactants, which have no charges but strong dipole moments and are strongly hydrated in aqueous solution.

The term zwitterionic surfactants is used to describe those surface-active compounds that carry at least one quaternary ammonium group and at least one —COO$^{(-)}$ or —SO$_3^{(-)}$ group in the molecule. Particularly suitable zwitterionic surfactants are the so-called betaines such as the N-alkyl-N,N-dimethylammonium glycinates, for example the cocoalkyl dimethylammonium glycinate, N-acyl-aminopropyl-N,N-dimethylammonium glycinates, for example the cocoacylaminopropyl dimethylammonium glycinate, and 2-alkyl-3-carboxymethyl-3-hydroxyethyl imidazolines each having about 8 to about 18 carbon atoms in the alkyl or acyl group, and the cocoacylaminoethyl hydroxyethyl carboxymethyl glycinate. A preferred zwitterionic surfactant is the fatty acid amide derivative known under the INCI name Cocamidopropyl Betaine.

Ampholytic surfactants are surface-active compounds which, in addition to a $C_8$-$C_{24}$ alkyl or acyl group in the molecule, contain at least one free amino group and at least one —COOH or —SO$_3$H group and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having about 8 to about 24 carbon atoms in the alkyl group. Typical examples of amphoteric or zwitterionic surfactants are alkyl betaines, alkylamidobetaines, amino propionates, aminoglycinates, imidazolinium betaines and sulfobetaines.

Particularly preferred ampholytic surfactants are N-cocosalkylaminopropionate, cocosacylaminoethylaminopropionate and $C_{12}$-$C_{18}$-acylsarcosine.

The agents may also additionally contain at least one nonionic surfactant. Suitable nonionic surfactants are alkyl polyglycosides as well as alkylene oxide addition products to fatty alcohols and fatty acids, each with about 2 to about 30 moles of ethylene oxide per mole of fatty alcohol or fatty acid, respectively. Preparations with good properties are also obtained if they contain, as nonionic surfactants, fatty acid esters of ethoxylated glycerol reacted with at least about 2 moles of ethylene oxide.

Furthermore, the agents may also additionally contain at least one cationic surfactant. Cationic surfactants are surfactants, i.e. surface-active compounds, each with one or more positive charges. Cationic surfactants contain only positive charges. Typically, these surfactants are composed of a hydrophobic moiety and a hydrophilic head group, with the hydrophobic moiety usually including a hydrocarbon backbone (e.g., comprising one or two linear or branched alkyl chains), and the positive charge(s) located in the hydrophilic head group. Examples of cationic surfactants are
- quaternary ammonium compounds which may carry one or two alkyl chains with a chain length of about 8 to about 28 carbon atoms as hydrophobic radicals,
- quaternary phosphonium salts substituted by one or more alkyl chains having a chain length of about 8 to about 28 carbon atoms or
- tertiary sulfonium salts.

Furthermore, the cationic charge can also be part of a heterocyclic ring (e.g. an imidazolium ring or a pyridinium ring) in the form of an onium structure. In addition to the functional unit carrying the cationic charge, the cationic surfactant may also contain other uncharged functional groups, as is the case, for example, with esterquats. The cationic surfactants are used in a total amount of about 0.1 to about 45% by weight, preferably about 1 to about 30% by weight and very preferably about 1 to about 15% by weight—based on the total weight of the respective agent.

Furthermore, the agents may also contain at least one anionic surfactant. Anionic surfactants are surface-active agents with exclusively anionic charges (neutralized by a corresponding counter cation). Examples of anionic surfactants are fatty acids, alkyl sulfates, alkyl ether sulfates and ether carboxylic acids with about 12 to about 20 C atoms in the alkyl group and up to about 16 glycol ether groups in the molecule.

The anionic surfactants are used in a total amount of about 0.1 to about 45% by weight, preferably about 1 to about 30% by weight and very preferably about 1 to about 15% by weight—based on the total weight of the respective agent.

Agent (a) and/or agent (b) may further comprise a matting agent. Suitable matting agents include, for example, (modified) starches, waxes, talc and/or (modified) silicas. The amount of matting agent is preferably between about 0.1 and about 10% by weight based on the total amount of agent (a) or agent (b). Preferably, agent (a) contains a matting agent.

The agent (a) and/or the agent (b) may further comprise a thickening agent.

When using agents (a) and/or (b), they must not be too thin and drip off the keratin material. For this reason, it may be preferred that the agent (a) and/or (b) contains a thickening agent.

In the context of one embodiment, a process for dyeing keratinous material is thus preferred, which is exemplified in that the agent (a) and/or the agent (b) further comprises a thickening agent.

Suitable thickeners include, for example, chemically modified celluloses, such as propyl cellulose, methyl ethyl cellulose, carboxymethyl cellulose, hydroxyethyl cellulose, methyl hydroxyethyl cellulose, ethyl hydroxyethyl cellulose, hydroxypropyl cellulose, Hydroxypropylmethylcellulose, carboxymethylhydroxyethylcellulose, sulfoethylcellulose, carboxymethylsulfoethylcellulose, hydroxypropylsulfoethylcellulose, hydroxyethylsulfoethylcellulose, methylethylhydroxyethylcellulose, methlylsulfoethylcellulose and/or ethylsulfoethylcellulose.

In a preferred embodiment, a method for dyeing keratinous material is exemplified in that the agent (a) and/or the agent (b) further comprises a thickening agent selected from the group of propylcellulose, methyl ethylcellulose, carboxymethylcellulose, hydroxyethylcellulose, methylhydroxyethylcellulose, Ethylhydroxyethylcellulose, hydroxypropylcellulose, hydroxypropylmethylcellulose, carboxymethylhydroxyethylcellulose, sulfoethylcellulose, carboxymethylsulfoethylcellulose, hydroxypropylsulfoethylcellulose, hydroxyethylsulfoethylcellulose, methylethythydroxyethylcellulose, methlylsulfoethylcellulose, ethylsulfethylcellulose, and mixtures thereof.

Particularly suitable thickeners are selected from hydroxyethyl cellulose, hydroxypropyl cellulose, hydroxypropyl methyl cellulose and mixtures thereof.

In a particularly preferred embodiment, a method for dyeing keratinous material is exemplified in that the agent (a) and/or the agent (b) further comprises a thickening agent selected from the group of hydroxyethylcellulose, hydroxypropylcellulose, hydroxypropylmethylcellulose and mixtures thereof.

Other suitable thickeners include galactomannans. Preferred galactomannans include galactomannans having the INCI name *Cyamopsis tetragonoloba* gum (Guar Gum), galactomannans having the INCI name *Ceratonia siliqua* (Carob) Gum (Locust Bean Gum), galactomannans having the INCI name *Cassia* Gum, and galactomannans having the INCI name *Caesalpinia spinosa* Gum (Tara Gum).

Accordingly, a process for dyeing keratinous material is particularly preferred, wherein agent (a) and/or agent (b) further comprises at least one galactomannan selected from the group of galactomannans having the INCI name *Cyamopsis tetragonoloba* gum (Guar Gum), Galactomannans with INCI name *Ceratonia siliqua* (Carob) Gum (Locust Bean Gum), galactomannans with INCI name *Cassia* Gum and galactomannans with INCI name *Caesalpinia spinosa* Gum (Tara Gum). In a particularly preferred embodiment, the galactomannan comprises a galactomannan having the INCI name *Caesalpinia spinosa* Gum (Tara Gum).

The amount of thickener is preferably between about 0.1 and about 10% by weight, in each case based on the total amount of agent (a) and/or agent (b).

The compositions may also contain other active ingredients, auxiliaries and additives, such as solvents; fatty ingredients such as $C_8$-$C_{30}$ fatty acid triglycerides, $C_8$-$C_{30}$ fatty acid monoglycerides, $C_8$-$C_{30}$ fatty acid diglycerides and/or hydrocarbons; structurants such as glucose, maleic acid and lactic acid; hair-conditioning compounds such as phospholipids, for example lecithin and kephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; Polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; Fats and waxes such as fatty alcohols, beeswax, montan wax and kerosenes; swelling and penetrating agents such as glycerol, propylene glycol monoethyl ether, carbonates, hydrogen carbonates, guanidines, ureas and primary, secondary and tertiary phosphates; Opacifiers such as latex, styrene/PVP and styrene/acrylamide copolymers; pearlescing agents such as ethylene glycol mono- and distearate and PEG-3 distearate; and blowing agents such as propane-butane mixtures, $N_2O$, dimethyl ether, $CO_2$ and air.

The selection of these further substances will be made by the skilled person according to the desired properties of the agents. With regard to further optional components as well as the quantities of these components used, reference is expressly made to the relevant manuals known to the skilled person. The additional active ingredients and auxiliaries are preferably used in the preparations as contemplated herein in amounts of from about 0.0001 to about 25% by weight in each case, in particular from about 0.0005 to about 15% by weight, based on the total weight of the respective composition.

Process for Dyeing Keratinous Materials

In the process as contemplated herein, agents (a) and (b) are applied to the keratinous materials, in particular to human hair. Thus, agents (a) and (b) are the ready-to-use agents. Agents (a) and (b) are different from each other.

Agents (a) and (b) can in principle be applied simultaneously or successively, with successive application being preferred.

The best results were obtained when agent (a) was first applied to the keratinous materials in a first step and agent (b) was applied in a second step.

Quite particularly preferred, therefore, is a process for treating keratinous material, in particular for coloring keratinous material, in particular human hair, comprising the following steps in the order indicated:
  in a first step, applying an agent (a) to the keratinous material, the agent comprising (a):
  (a1) at least one organic silicon compound selected from the group of silanes having one, two or three silicon atoms,
  (a2) at least one hydroxycarboxylic acid ester and
  (a3) at least one diol
  in a second step, applying an agent (b) to the keratinous material, the agent comprising (b):
  (b1) at least one sealing reagent,
wherein at least one of the agents (a) and (b) further comprises at least one colorant compound selected from the group of pigments and/or direct dyes.

Moreover, in order to impart a high leaching resistance to the dyed keratinous material over a longer period of time, agents (a) and (b) are particularly preferably applied within one and the same dyeing process, which means that there is a period of a maximum of several hours between the application of agents (a) and (b).

In a further preferred embodiment, the method is exemplified in that agent (a) is applied first and agent (b) is applied thereafter, the period between the application of agents (a) and (b) being at most about 24 hours, preferably at most about 12 hours and particularly preferably at most about 6 hours.

A feature of the agent (a) is its content of at least one reactive organic silicon compound (a1). The reactive organic silicon compound(s) (a1) undergoes an oligomerization or polymerization reaction and thus functionalizes the hair surface as soon as it comes into contact with it. In this way, a first, film is formed. The hydroxycarboxylic acid ester (a2) is incorporated into the film. In the second step of the process, a second agent (b) is now applied to the hair. During the application of the agent (b), comprising at least one film-forming polymer as sealing reagent (b1), the latter interacts with the silane film and is thus bound to the keratinous materials. During the application of agent (b) comprising at least one alkalizing agent or acidifying agent as sealing reagent (b1), the formation of the silane film is positively influenced. The desired coloring of the keratinous material is achieved by employing the coloring compound in agent (a) and/or in agent (b). The coloration can be achieved by a colored silane film (the colorant compound is only in agent (a)), by a colored polymer film (the coloring compound is only in agent (b) and this contains a film-forming polymer as sealing reagent (b1)) or by a colored silane film and by a colored polymer film (agents (a) and (b) each contain at least one coloring compound and agent (b) contains a film-forming polymer as sealing reagent (b1)).

In the context of a further embodiment, a method is very particularly preferred, comprising the following steps in the order indicated
  (1) Application of the agent (a) on the keratinous material,
  (2) Allowing the agent (a) to act for a period of about 10 seconds to about 10 minutes, preferably from about 10 seconds to about 5 minutes,
  (3) if necessary, rinsing the keratinous material with water,
  (4) Application of the agent (b) on the keratinous material, (5) Allowing the agent (b) to act for a period of about 30 seconds to about 30 minutes, preferably from about 30 seconds to about 10 minutes, (6) Rinse the keratinous material with water.

By rinsing the keratinous material with water in steps (3) and (6) of the process, it is understood as contemplated herein that only water is used for the rinsing process, without the use of other agents different from agents (a) and (b).

In step (1), agent (a) is first applied to the keratinous materials, in particular human hair. If the agent (a) is prepared water-free or low in water, i.e. if the agent contains less than about 5% by weight of water, based on the total amount of agent (a), it is essential for an optimum dyeing result that agent (a) is applied to moist keratinous material, in particular moist human hair.

After application, the agent (a) is left to act on the keratinous materials. In this context, exposure times of about 10 seconds to about 10 minutes, preferably about 20 seconds to about 5 minutes and most preferably about 30 seconds to about 2 minutes on the hair have proven to be particularly advantageous.

In a preferred embodiment of the process, the agent (a) can now be rinsed from the keratinic materials before the agent (b) is applied to the hair in the subsequent step.

Stains with equally good wash fastness were obtained when agent (b) was applied to the keratinous materials that were still exposed to agent (a).

In step (4), agent (b) is now applied to the keratinous materials. After application, the agent (b) is now left to act on the hair.

Even with a short contact time of the agent (b), the process allows the production of dyeings with particularly good intensity and wash fastness. Exposure times of about 10 seconds to about 10 minutes, preferably about 20 seconds to about 5 minutes and most preferably about 30 seconds to about 3 minutes on the hair have proven to be particularly advantageous.

In step (6), the agent (b) (and any agent (a) still present) is now rinsed out of the keratinous material with water.

In this embodiment, the sequence of steps (1) to (6) preferably takes place within about 24 hours.

Agent (a) contains, with the organic silicon compound(s), a class of highly reactive compounds that can undergo hydrolysis or oligomerization and/or polymerization when used. As a result of their high reactivity, these organic silicon compounds form a film on the keratinous material.

To avoid premature oligomerization or polymerization, it is of considerable advantage to the user to prepare the ready-to-use agent (a) only shortly before application.

In yet another embodiment, preferred is a method comprising the following steps in the order indicated (1) Preparation of an agent (a) by mixing a first agent (a'), a second agent (a''') and a third agent (a''), wherein
the first agent (a') comprises at least one organic silicon compound (a1) from the group of silanes having one, two or three silicon atoms,
the second agent (a'') comprises at least one hydroxycarboxylic acid ester (a2) and at least one colorant compound selected from the group of pigments and/or direct dyes, and the third agent (a''') contains at least one diol, (2) Application of the agent (a) on the keratinous material, (3) Allowing the agent (a) to act for a period of about 10 seconds to about 10 minutes, preferably from about 10 seconds to about 5 minutes, (4) if necessary, rinsing the keratinous material with water, (5) Application of the agent (b) on the keratinous material, (6) Allowing the agent (b) to act for a period of about 30 seconds to about 30 minutes, preferably from about 30 seconds to about 10 minutes, (7) Rinse the keratinous material with water.

In order to be able to provide a formulation that is as stable as possible in storage, the agent (a') itself is preferably formulated to be low in water or water-free.

In a preferred embodiment, a process is exemplified in that the agent (a')—based on the total weight of the agent (a')—contains a water content of from about 0.001 to about 10% by weight, preferably from about 0.5 to about 9% by weight, more preferably from about 1 to about 8% by weight and very particularly preferably from about 1.5 to about 7% by weight.

The agent (a''') may contain water.

The agent (a''') may further comprise a thickening agent. Within this embodiment, it is preferred that the agent (a'') comprises a thickening agent selected from the group of hydroxyethylcellulose, hydroxypropylcellulose, hydroxypropylmethylcellulose, and mixtures thereof.

Within this embodiment, the ready-to-use agent (a) is prepared by mixing agents (a'), (a'') and (a''').

For example, the user may first stir or shake the agent (a') containing the organic silicon compound(s) (a1) with the hydroxycarboxylic ester-containing agent (a'') and the diol-containing agent (a'''). The user can now apply this mixture of (a'), (a'') and (a''') to the keratinous materials—either immediately after its preparation or after a short reaction time of about 10 seconds to about 30 minutes. Subsequently, the user can apply the agent (b) as previously described.

Alternatively, the user may first stir or shake the agent (a') containing the organic silicon compound(s) (a1) with the hydroxycarboxylic acid ester-containing agent (a'') and the diol-containing agent (a'''). The user can then mix this mixture of (a'), (a'') and (a''') with a predetermined amount of water, for example tap water or a fourth, water-containing agent (a''''), and now apply it to the keratinous materials—either immediately after its preparation or after a short reaction time of about 10 seconds to about 30 minutes. Subsequently, the user can apply the agent (b) as previously described.

In a further alternative, if the agent (a''') already contains significant amounts of water, the user can stir or shake the agent (a') containing the organic silicon compound(s) (a1) with the hydroxycarboxylic ester-containing agent (a'') and the water- and diol-containing agent (a'''). This mixture of (a'), (a'') and (a''') can be applied by the user and now—either directly after its preparation or after a short reaction time of about 10 seconds to about 30 minutes—to the keratinous materials. Subsequently, the user can apply the agent (b) as previously described.

It may be preferred if the process further employs a water-containing agent (a'''') that contains at least about 10% by weight of water, based on the total weight of agent (a'''').

In a preferred embodiment, a process is exemplified in that an agent (a'''') is used which—based on the total weight of the agent (a'''')—has a water content of from about 10 to about 99.9% by weight, preferably from about 20 to about 99% by weight, more preferably from about 30 to about 95% by weight and very particularly preferably from about 35 to about 90% by weight.

In the context of a further embodiment, particularly preferred is a method comprising the following steps in the order indicated (1) Preparation of an agent (a) by mixing a first agent (a'), a second agent (a'') and a third agent (a''), wherein the first agent (a') comprises at least one organic silicon compound (a1) from the group of silanes having one, two or three silicon atoms,
the second agent (a") comprises at least one hydroxycarboxylic acid ester (a2), and
the third agent (a''') comprises a diol and, if desired, at least one colorant compound selected from the group of pigments and/or direct dyes,
(2) Application of the agent (a) on the keratinous material,
(3) Allowing the agent (a) to act for a period of about 10 seconds to about 10 minutes, preferably from about 10 seconds to about 5 minutes,
(4) if necessary, rinsing the keratinous material with water,
(5) Application of the agent (b) on the keratinous material,
(6) Allowing the agent (b) to act for a period of about 30 seconds to about 30 minutes, preferably from about 30 seconds to about 10 minutes,
(7) Rinse the keratinous material with water.

Also within this embodiment, the ready-to-use agent (a) is prepared by mixing agents (a'), (a") and (a''').

For example, the user can stir or shake the agent (a') containing the organic silicon compound(s) (a1) first with the hydroxycarboxylic ester-containing agent (a") and then with the diol-containing agent (a'''). The user can now apply this mixture of (a'), (a") and (a''') to the keratinous materials—either immediately after its preparation or after a short reaction time of about 10 seconds to about 30 minutes. Subsequently, the user can apply the agent (b) as previously described.

Also within this embodiment, it may be preferred if a water-containing agent (a'''') containing at least about 10% by weight of water, based on the total weight of agent (a''''), is further used to prepare the ready-to-use agent (a). The ready-to-use agent (a) is then prepared by mixing agents (a'), (a"), (a''') and (a'''').

Multicomponent Packaging Unit (Kit-of-Parts)

To increase user convenience, the user is preferably provided with all the necessary articles in the form of a multi-component packaging unit (kit-of-parts).

A second object of the present disclosure is therefore a multi-component packaging unit (kit-of-parts) for dyeing keratinous material, comprising separately prepared
a first container comprising an agent (a'), wherein the agent comprises (a'):
(a1) at least one organic silicon compound selected from the group of silanes having one, two or three silicon atoms, and
a second container comprising an agent (a"), wherein the agent comprises (a"):
(a2) at least one hydroxycarboxylic acid ester,
a third container comprising an agent (a'''), said agent comprising (a'''):
(a3) at least one diol, and
a fourth container containing agent (b), wherein the agent contains (b):
(b1) at least one sealing reagent,
where the components (a1), (a2), (a3) and (b1) have been disclosed in detail above, and at least one of the agents (a"), (a''') and (b) further comprises at least one colorant compound selected from the group of pigments and/or direct dyes.

A third object of the present disclosure is a multi-component packaging unit (kit-of-parts) for dyeing keratinous material, comprising separately prepared
a first container comprising an agent (a'), wherein the agent comprises (a'):
(a1) at least one organic silicon compound selected from the group of silanes having one, two or three silicon atoms, and
a second container comprising an agent (a"), wherein the agent comprises (a"):
(a2) at least one hydroxycarboxylic acid ester, and
a third container comprising an agent (a'''), said agent comprising (a'''):
(a3) at least one diol and at least about 30% by weight, based on the total weight of agent (a"), of water, and
a fourth container containing agent (b), wherein the agent contains (b):
(b1) at least one sealing reagent,
where the components (a1), (a2), (a3) and (b1) have been disclosed in detail above, and at least one of the agents (a"), (a''') and (b) further comprises at least one colorant compound selected from the group of pigments and/or direct dyes.

The organic silicon compounds (a1) from the group of silanes with one, two or three silicon atoms contained in the agent (a') of the kits correspond to the organic silicon compounds (a1) that were also used in the agent (a) of the previously described process.

The hydroxycarboxylic acid ester (a2) contained in the agent (a") of the kits corresponds to the hydroxycarboxylic acid ester (a2) that was also used in the agent (a) of the previously described process.

The diol (a3) contained in the agent (a''') of the kits corresponds to the diol (a3) that was also used in the agent (a) of the previously described process.

The sealing reagent (b1) contained in agent (b) of the kits corresponds to sealing reagent (b1) that was also used in agent (b) of the previously described method.

In a further preferred embodiment, a multi-component packaging unit (kit-of-parts) for dyeing keratinous material, comprising separately prepared
a first container comprising an agent (a'), wherein the agent comprises (a'):
at least one organic silicon compound (a1) from the group of silanes having one, two or three silicon atoms, and
a second container comprising an agent (a"), wherein the agent comprises (a"):
(a2) at least one hydroxycarboxylic acid ester and a coloring compound selected from the group of pigments and/or direct dyes,
a third container comprising an agent (a'''), said agent comprising (a'''):
(a3) at least one diol, and
a fourth container containing agent (b), wherein the agent contains (b):
(b1) at least one sealing reagent,
wherein the components (a1), (a2), (a3) and (b1) have been disclosed in detail above.

In a further preferred embodiment, a multi-component packaging unit (kit-of-parts) for dyeing keratinous material, comprising separately prepared
a first container comprising an agent (a'), wherein the agent comprises (a'):
at least one organic silicon compound (a1) from the group of silanes having one, two or three silicon atoms, and
a second container comprising an agent (a"), wherein the agent comprises (a"):

(a2) at least one hydroxycarboxylic acid ester,
a third container comprising an agent (a'''), said agent comprising (a'''):
(a3) at least one diol, and
a fourth container containing agent (b), wherein the agent contains (b):
(b1) at least one sealing reagent comprising a film-forming polymer, and further a coloring compound selected from the group of pigments and/or direct dyes,
wherein the components (a1), (a2), (a3) and (b1) have been disclosed in detail above.

In the context of still another embodiment, preferred is a multi-component packaging unit (kit-of-parts) for dyeing keratinous material, comprising separately prepared
a first container comprising an agent (a'), wherein the agent comprises (a'):
at least one organic silicon compound (a1) from the group of silanes having one, two or three silicon atoms, and
a second container comprising an agent (a''), wherein the agent comprises (a''):
(a2) at least one hydroxycarboxylic acid ester and at least one colorant compound selected from the group of pigments and/or direct dyes,
a third container comprising an agent (a'''), said agent comprising (a'''):
(a3) at least one diol,
a fourth container containing an agent (b'), wherein the agent contains (b'):
(b1) at least one sealing reagent comprising a film-forming polymer, and
a fifth container comprising an agent (b''), wherein the agent comprises (b'):
(b2) at least one colorant compound selected from the group of pigments and/or direct dyes,
wherein the components (a1), (a2), (a3), (b1) and (b2) have been disclosed in detail above.

In this embodiment, the ready-to-use agent (b) is prepared by mixing agents (b') and (b'').

In the context of still another embodiment, preferred is a multi-component packaging unit (kit-of-parts) for dyeing keratinous material, comprising separately prepared
a first container comprising an agent (a'), wherein the agent comprises (a'):
at least one organic silicon compound (a1) from the group of silanes having one, two or three silicon atoms, and
a second container comprising an agent (a''), wherein the agent comprises (a''):
(a2) at least one hydroxycarboxylic acid ester and at least one colorant compound selected from the group of pigments and/or direct dyes,
a third container comprising an agent (a'''), said agent comprising (a'''):
(a3) at least one diol and at least about 30% by weight, based on the total weight of agent (a''), of water,
a fourth container containing an agent (b'), wherein the agent contains (b'):
(b1) at least one sealant reagent comprising a film-forming polymer, and
a fifth container comprising an agent (b''), wherein the agent comprises (b'):
(b2) at least one colorant compound selected from the group of pigments and/or direct dyes,
wherein the components (a1), (a2), (a3), (b1) and (b2) have been disclosed in detail above.

In this embodiment, the ready-to-use agent (b) is prepared by mixing agents (b') and (b'').

In the context of still another embodiment, preferred is a multi-component packaging unit (kit-of-parts) for dyeing keratinous material, comprising separately prepared
a first container comprising an agent (a'), wherein the agent comprises (a'):
at least one organic silicon compound (a1) from the group of silanes having one, two or three silicon atoms, and
a second container comprising an agent (a''), wherein the agent comprises (a''):
(a2) at least one hydroxycarboxylic acid ester,
a third container comprising an agent (a'''), said agent comprising (a'''):
(a3) at least one diol,
a fourth container containing an agent (b'), wherein the agent contains (b'):
(b1) at least one sealing reagent comprising a film-forming polymer, and
a fifth container comprising an agent (b''), wherein the agent comprises (b'):
(b2) at least one colorant compound selected from the group of pigments and/or direct dyes,
wherein the components (a1), (a2), (a3), (b1) and (b2) have been disclosed in detail above.

In this embodiment, the ready-to-use agent (b) is prepared by mixing agents (b') and (b'').

It may be preferred in this embodiment that one of the agents (a'') and (a''') further comprises at least one colorant compound selected from the group of pigments and/or direct dyes.

In any embodiment of the multi-component packaging unit, it may be preferred that the agents (a''), (a''') and/or (b) further comprise a thickening agent. Particularly preferably, the agents (a''') and/or (b) further comprise a thickening agent.

According to this embodiment, a multicomponent packaging unit (kit-of-parts) is preferred, wherein the agent (a'') comprises a thickening agent selected from the group of hydroxyethylcellulose, hydroxypropylcellulose, hydroxypropylmethylcellulose and mixtures thereof.

A kit-of-parts is further preferred wherein the agent (b) comprises a thickening agent selected from the group of ethyl cellulose, hydroxypropyl cellulose, hydroxypropyl methyl cellulose, and mixtures thereof.

A multicomponent kit-of-parts is also preferred, wherein the agent (a'') and the agent (b) comprise a thickening agent selected from the group of hydroxyethylcellulose, hydroxypropylcellulose, hydroxypropylmethylcellulose and mixtures thereof.

Oligo and polymerization reactions of the organic silicon compound (a1) are already initiated when agents (a') and (a'') are mixed or when agents (a'), (a'') and (a''') are mixed.

It has proved to be a major challenge to optimally adjust the oligo and polymerization rate of the organic silicon compound (a1), i.e. the rate at which the silane film forms on the keratin material, to the application conditions.

When applied to human hair, for example, too fast an oligo and polymerization rate will result in polymerization being completed before all hair sections have been treated. Polymerization that is too fast makes whole-head treatment impossible. In the dyeing process, the excessively fast polymerization manifests itself in an uneven color result, so that the batches that were treated last are only poorly colored.

On the other hand, if polymerization is too slow, all areas of the keratin material can be treated without time pressure, but this increases the application time.

Surprisingly, it has been shown that the presence of a hydroxycarboxylic acid ester and a diol in the agent (a) leads not only to improved adhesion of the colorant compound to the keratinous material, but also to an optimal oligo and polymerization rate of the organic silicon compound (a1). This not only leads to expedient application times, but also the durability of the coloring as well as its haptics are significantly improved.

Concerning the further preferred embodiments of the multicomponent packaging unit, mutatis mutandis what has been said about the process applies.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A method for dyeing keratinous material, the method comprising the steps of:
   applying an agent (a) to the keratinous material, wherein the agent (a) comprises:
   (a1) an organic silicon compound selected from the group of silanes having one, two or three silicon atoms,
   (a2) a hydroxycarboxylic acid ester, and
   (a3) a diol and
   applying an agent (b) to the keratinous material, wherein the agent (b) comprises:
   (b1) a sealing reagent,
   wherein at least one of the agents (a) and (b) further comprises at least one colorant compound selected from the group of pigments and/or direct dyes.

2. The method according to claim 1, wherein the agent (a) comprises the organic silicon compound (a1) of a formula (I) and/or a formula (II)

$$R_1R_2N\text{-}L\text{-}Si(OR_3)_a(R_4)_b \quad (I),$$

where
   $R_1$, $R_2$ independently represent a hydrogen atom or a $C_1$-$C_6$ alkyl group,
   L is a linear or branched, divalent $C_1$-$C_{20}$ alkylene group,
   $R_3$, $R_4$ are independent of each other and represent a $C_1$-$C_6$ alkyl group,
   a represents an integer from 1 to 3, and
   b is the integer 3-a, and
   wherein in the organic silicon compound of formula (II)

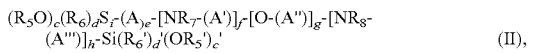

$$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad (II),$$

wherein
   R5, R5', R5", R6, R6' and R6" independently represent a $C_1$-$C_6$ alkyl group,
   A, A', A", A'" and A"" independently represent a linear or branched $C_1$-$C_{20}$ divalent alkylene group,
   $R_7$ and $R_8$ independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of formula (III)

$$(A'''')\text{-}Si(R_6'')_{d''}(OR_5'')_{c''} \quad (III),$$

wherein
   c stands for an integer from 1 to 3,
   d stands for the integer 3-c,
   c' stands for an integer from 1 to 3,
   d' stands for the integer 3-c',
   c" stands for an integer from 1 to 3,
   d" stands for the integer 3-c",
   e stands for 0 or 1,
   f stands for 0 or 1,
   g stands for 0 or 1,
   h stands for 0 or 1,
   with the proviso that at least one of the radicals from e, f, g and h is different from 0.

3. The method according to claim 2, wherein the agent (a) comprises the organic silicon compound (a1) of the formula (I),

$$R_1R_2N\text{-}L\text{-}Si(OR_3)_a(R_4)_b \quad (I),$$

where
   $R_1$, and $R_2$ both represent a hydrogen atom,
   L is a linear, divalent $C_1$-$C_6$ alkylene group,
   $R_3$, and $R_4$ independently represent a methyl group or an ethyl group,
   a stands for number 3 and
   b stands for number 0.

4. The method according to claim 2, wherein the agent (a) comprises the organic silicon compound (a1) of the formula (I) selected from the group of
   (3-Aminopropyl)triethoxysilane
   (3-Aminopropyl)trimethoxysilane
   1-(3-aminopropyl)silanetriol
   (2-Aminoethyl)triethoxysilane
   (2-Aminoethyl)trimethoxysilane
   1-(2-aminoethyl)silanetriol
   (3-Dimethylaminopropyl)triethoxysilane
   (3-Dimethylaminopropyl)trimethoxysilane
   1-(3-Dimethylaminopropyl)silanetriol
   (2-dimethylaminoethyl)triethoxysilane
   (2-dimethylaminoethyl)trimethoxysilane
   1-(2-dimethylaminoethyl)silanetriol, and
   combinations thereof.

5. The method according to claim 2, wherein the agent (a) comprises the organic silicon compound (a1) of the formula (II),

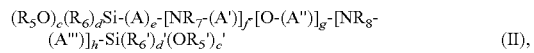

$$(R_5O)_c(R_6)_dSi\text{-}(A)_e\text{-}[NR_7\text{-}(A')]_f\text{-}[O\text{-}(A'')]_g\text{-}[NR_8\text{-}(A''')]_h\text{-}Si(R_6')_{d'}(OR_5')_{c'} \quad (II),$$

where
   e and f both stand for number 1,
   g and h both stand for number 0,
   A and A' independently of one another represent a linear, divalent C1-C6 alkylene group, and
   R7 represents a hydrogen atom, a methyl group, a 2-hydroxyethyl group, a 2-alkenyl group, a 2-aminoethyl group or a group of formula (III).

6. The method according to claim 1, wherein the agent (a) comprises the organic silicon compound (a1) of a formula (IV),

$$R_9Si(OR_{10})_k(R_{11})_m \quad (IV),$$

where $R_9$ stands for a $C_1$-$C_{18}$ alkyl group, $R_{10}$ represents a hydrogen atom or a $C_1$-$C_6$ alkyl group, $R_{11}$ stands for a $C_1$-$C_6$ alkyl group k is an integer from 1 to 3, and m stands for the integer 3-k.

7. The method according to claim 6, wherein the agent (a) comprises the organic silicon compound (a1) of the formula (IV) selected from the group of:

Methyltrimethoxysilane
Methyltriethoxysilane
Ethyltrimethoxysilane
Ethyltriethoxysilane
Propyltrimethoxysilane
Propyltriethoxysilane
Hexyltrimethoxysilane
Hexyltriethoxysilane
Octyltrimethoxysilane
Octyltriethoxysilane
Dodecyltrimethoxysilane,
Dodecyltriethoxysilane,
Octadecyltrimethoxysilane,
Octadecyltriethoxysilane and
Mixtures thereof.

8. The method according to claim 1, wherein the agent (a) comprises at least two structurally different organic silicon compounds (a1).

9. The method of claim 8, wherein the sealing reagent comprises a compound selected from the group of film-forming polymers, alkalizing agents, acidifying agents, and mixtures thereof.

10. The method according to claim 1, wherein the agent (a) comprises citric acid triethyl ester as the hydroxycarboxylic acid ester (a2).

11. The method according to claim 1, wherein the agent (a) comprises the diol (a3) selected from the group of ethylene glycol, 1,2-propylene glycol, 1,3-propylene glycol, and combinations thereof.

12. The method according to claim 1, wherein the agent (a) and the agent (b) each further comprise at least one colorant compound selected from the group of pigments and/or direct dyes.

13. The method according to claim 1, wherein the agent (b) further comprises a colorant compound selected from the group of pigments and/or direct dyes comprising at least one pigment selected from the group of lamellar metallic substrate platelet-based pigments, lenticular metallic substrate platelet-based pigments, vacuum metallized pigment (VMP), lenticular metallic substrate platelet, pigments based on a metallic substrate platelet comprising "vacuum metallized pigment" (VMP), pigments based on natural or synthetic mica coated with at least one metal oxide, pigments based on natural or synthetic mica coated with a metal oxychloride, and combinations thereof.

14. The method according to claim 1, wherein the agent (a) further comprises a coloring compound selected from the group of pigments and/or direct dyes comprising at least one pigment selected from the group of carmine, quinacridone, phthalocyanine, sorghum, blue pigments having the color index numbers CI 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers 11725, CI 15510, CI 45370, CI 71105, red pigments with the color index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, CI 75470, colored metal oxides, metal hydroxides, metal oxide hydrates, silicates, metal sulfides, complex metal cyanides, metal sulfates, bronze pigments and mixtures thereof;

and wherein the composition (b) further comprises a coloring compound selected from the group of pigments and/or direct-acting dyes which comprises at least one pigment selected from the group of pigments based on a lamellar metallic substrate platelet, pigments based on a lenticular metallic substrate platelet, pigments based on a metallic substrate platelet comprising "vacuum metallized pigment" (VMP), pigments based on mica coated with a metal oxide, pigments based on mica coated with metal oxychloride, and mixtures thereof.

15. A multi-component packaging unit (kit-of-parts) for dyeing keratinous material, comprising:

a first container containing an agent (a'), wherein the agent (a') comprises:

an organic silicon compound (a1) selected from the group of silanes having one, two or three silicon atoms, and a second container containing an agent (a"), wherein the agent (a") comprises:

a hydroxycarboxylic acid ester (a2), a third container containing an agent (a'''), said agent (e) comprising:

a diol (a3), and a fourth container containing agent (b), wherein the agent (b) comprises:

a sealing reagent (b1), wherein at least one of the agents (a"), (a''') and (b) further comprises at least one colorant compound selected from the group of pigments and/or direct dyes.

16. The multi-component packaging unit (kit-of-parts) for dyeing keratinous material of claim 15, wherein:

the organic silicon compound (a1) comprises a compound of a formula (I) and/or a formula (II)

where $R_1$, $R_2$ independently represent a hydrogen atom or a $C_1$-$C_6$ alkyl group, L is a linear or branched, divalent $C_1$-$C_{20}$ alkylene group, $R_3$, $R_4$ are independent of each other and represent a $C_1$-$C_6$ alkyl group, a represents an integer from 1 to 3, and b is the integer 3-a, and wherein in the organic silicon compound of formula (II)

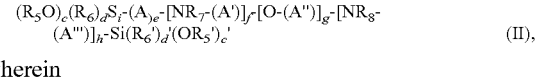

wherein

R5, R5', R5", R6, R6' and R6" independently represent a C1-C6 alkyl group,

A, A', A", A''' and A"" independently represent a linear or branched $C_1$-$C_{20}$ divalent alkylene group, R7 and R8 independently represent a hydrogen atom, a $C_1$-$C_6$ alkyl group, a hydroxy-$C_1$-$C_6$ alkyl group, a $C_2$-$C_6$ alkenyl group, an amino-$C_1$-$C_6$ alkyl group or a group of formula (III)

wherein
c stands for an integer from 1 to 3,
d stands for the integer 3-c,
c' stands for an integer from 1 to 3,
d' stands for the integer 3-c',
c" stands for an integer from 1 to 3,
d" stands for the integer 3-c",
e stands for 0 or 1,
f stands for 0 or 1,
g stands for 0 or 1,
h stands for 0 or 1,
with the proviso that at least one of the radicals from e, f, g and h is different from 0.

17. The multi-component packaging unit (kit-of-parts) for dyeing keratinous material of claim 15, wherein the organic silicon compound (a1) is selected from the group of:
(3-Aminopropyl)triethoxysilane
(3-Aminopropyl)trimethoxysilane
1-(3-aminopropyl)silanetriol
(2-Aminoethyl)triethoxysilane
(2-Aminoethyl)trimethoxysilane
1-(2-aminoethyl)silanetriol
(3-Dimethylaminopropyl)triethoxysilane
(3-Dimethylaminopropyl)trimethoxysilane
1-(3-Dimethylaminopropyl)silanetriol
(2-dimethylaminoethyl)triethoxysilane
(2-dimethylaminoethyl)trimethoxysilane
1-(2-dimethylaminoethyl)silanetriol, and mixtures thereof.

18. The multi-component packaging unit (kit-of-parts) for dyeing keratinous material of claim 15, wherein the agent (a) comprises the organic silicon compound (a1) of a formula (IV), $$R_9Si(OR_{10})_k(R_{11})_m \qquad (IV),$$

where
$R_9$ stands for a $C_1$-$C_{18}$ alkyl group,
$R_{10}$ represents a hydrogen atom or a $C_1$-$C_6$ alkyl group,
$R_{11}$ stands for a $C_1$-$C_6$ alkyl group
k is an integer from 1 to 3, and
m stands for the integer 3-k.

19. The multi-component packaging unit (kit-of-parts) for dyeing keratinous material of claim 15, wherein the agent (a) comprises at least two structurally different organic silicon compounds (a1).

20. The multi-component packaging unit (kit-of-parts) for dyeing keratinous material of claim 15, wherein the agent (a) comprises the diol (a3) selected from the group of ethylene glycol, 1,2-propylene glycol, 1,3-propylene glycol, and combinations thereof.

* * * * *

UNITED STATES PATENT AND TRADEMARK OFFICE
CERTIFICATE OF CORRECTION

PATENT NO. : 11,883,518 B2
APPLICATION NO. : 17/785878
DATED : January 30, 2024
INVENTOR(S) : Rene Krohn et al.

It is certified that error appears in the above-identified patent and that said Letters Patent is hereby corrected as shown below:

In the Specification

Column 10, Line 25 change "$(R_5O)_c(R_6)_d\text{-}(A)_e\text{-}[NR_7\text{-}(A')]_f\text{-}[O(A'')]_g\text{-}[NR_8\text{-}(A''')]_h\text{-}Si(R_6')_{d'}(OR_5')_{e'}$" to -- $\text{-}(R_5O)_c(R_6)_d\text{-}(A)_e\text{-}[NR_7\text{-}(A')]_f\text{-}[O(A'')]_g\text{-}[NR_8\text{-}(A''')]_h\text{-}Si(R_6')_{d'}(OR_5')_{c'}$ --.

Column 11, Line 56 change "$(A'')\text{-}Si(R_6'')_{d''}(OR_5'')_{e'''}$" to -- $(A''')\text{-}Si(R_6'')_{d''}(OR_5'')_{c''}$ --.

Signed and Sealed this
Fourth Day of June, 2024

Katherine Kelly Vidal
*Director of the United States Patent and Trademark Office*